(12) United States Patent
Miyano

(10) Patent No.: US 9,395,515 B2
(45) Date of Patent: Jul. 19, 2016

(54) IMAGING OPTICAL SYSTEM AND IMAGING DEVICE

(71) Applicant: FUJIFILM Corporation, Tokyo (JP)

(72) Inventor: Hitoshi Miyano, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 616 days.

(21) Appl. No.: 13/868,568

(22) Filed: Apr. 23, 2013

(65) Prior Publication Data

US 2013/0235176 A1    Sep. 12, 2013

Related U.S. Application Data

(63) Continuation of application No. PCT/JP2011/074292, filed on Oct. 21, 2011.

(30) Foreign Application Priority Data

Oct. 25, 2010    (JP) .................. 2010-238619

(51) Int. Cl.
*G02B 9/58*    (2006.01)
*G02B 13/04*    (2006.01)
(Continued)

(52) U.S. Cl.
CPC .............. *G02B 9/58* (2013.01); *A61B 1/00096* (2013.01); *G02B 13/04* (2013.01); *G02B 13/06* (2013.01);
(Continued)

(58) Field of Classification Search
CPC .............. G02B 9/34; G02B 9/58; G02B 9/60; G02B 9/62; G02B 9/64; G02B 13/0045; G02B 13/005; G02B 13/006; G02B 13/04; G02B 13/06; G02B 23/24; G02B 23/2407; G02B 23/243; G02B 23/2484; A61B 1/00096

USPC .......................................................... 359/782
See application file for complete search history.

(56) References Cited

U.S. PATENT DOCUMENTS 4,083,628 A * 4/1978 Koizumi ................ G02B 13/24
                                                                    359/782
4,674,844 A    6/1987 Nishioka et al.
(Continued)

FOREIGN PATENT DOCUMENTS

JP    4-335609    11/1992
JP    8-313803    11/1996
(Continued)

OTHER PUBLICATIONS

Translation of the International Preliminary Report on Patentability issued by the PCT International Bureau on Apr. 25, 2013 in PCT International Application No. PCT/JP2011/074292, 5 pages.

*Primary Examiner* — Jordan Schwartz
(74) *Attorney, Agent, or Firm* — Young & Thompson

(57) ABSTRACT

An imaging optical system comprises a first lens group composed of a negative single lens, a second lens group composed of a positive lens element and a negative lens element attached together, an aperture stop, a third lens group composed of a positive lens element and a negative lens element attached together, and a fourth lens group composed of a negative single lens, in this order from an object side. Expressions $0.37 < hF/IH < 0.5$ and $0.37 < hR/IH < 0.5$ are satisfied where "IH" denotes a maximum image height on an image plane, "hF" denotes an incident height of a principal ray, directed to a position of the maximum image height on the image plane, at its entrance into the first lens group, and "hR" denotes an exit height of the principal ray at its exit from the fourth lens group.

7 Claims, 14 Drawing Sheets

(51) Int. Cl.
  *G02B 13/06* (2006.01)
  *G02B 23/24* (2006.01)
  *G03B 17/00* (2006.01)
  *G03B 37/00* (2006.01)
  *A61B 1/00* (2006.01)

(52) U.S. Cl.
  CPC .......... *G02B 23/243* (2013.01); *G02B 23/2484* (2013.01); *G03B 17/00* (2013.01); *G03B 37/005* (2013.01)

(56) References Cited

U.S. PATENT DOCUMENTS

| | | | |
|---|---|---|---|
| 5,781,350 A * | 7/1998 | Tachihara | G02B 23/243 359/660 |
| 5,805,359 A | 9/1998 | Yamanashi | |
| 7,746,572 B2 | 6/2010 | Asami | |
| 2006/0007561 A1* | 1/2006 | Suzuki | G02B 13/06 359/749 |
| 2009/0052061 A1 | 2/2009 | Asami | |
| 2012/0176527 A1* | 7/2012 | Chen | G02B 13/004 348/340 |
| 2012/0194922 A1* | 8/2012 | Tang | G02B 9/34 359/716 |
| 2012/0262804 A1* | 10/2012 | Tang | G02B 13/004 359/717 |

FOREIGN PATENT DOCUMENTS

| | | |
|---|---|---|
| JP | 2008-116877 | 5/2008 |
| JP | 2009-47947 | 3/2009 |

\* cited by examiner

IMAGING OPTICAL SYSTEM AND IMAGING DEVICE

BACKGROUND OF THE INVENTION

1. Field of the Invention

The present invention relates to a wide angle imaging optical system used with a solid state image sensor, and more particularly to an imaging optical system with a small outer diameter and a short total length relative to a maximum image height and to an imaging device using the imaging optical system and an image sensor.

2. Description Related to the Prior Art

Various imaging devices comprising a CCD image sensor or a CMOS image sensor and an imaging optical system are known. The imaging optical system has lens groups and an aperture stop. Wide angle imaging optical systems are commonly used in the imaging devices for monitoring or observation purposes. It is essential for the imaging device incorporated in a mobile terminal such as a mobile phone or a distal end portion of an endoscope to be compact. For example, a nasal endoscope has been put into practical use, instead of a peroral endoscope, to reduce physical stress on a patient when the endoscope is inserted. An outer diameter of the distal end portion of the peroral endoscope is reduced to in the order of 9 mm. An outer diameter of the distal end portion of the nasal endoscope is reduced to less than 6 mm. Accordingly, it is indispensable to downsize the imaging device incorporated in the distal end portion.

A cylindrical rigid tip section is provided in the distal end portion of the endoscope. The length of the rigid tip section is in the order of 20 to 30 mm. A bendable flexible section is provided at the rear end of the rigid tip section. A direction of the rigid tip section is changed by operating an angle knob. The imaging device comprising the image sensor and the imaging optical system is incorporated in the rigid tip section. An image of a region of interest is captured through an objective window in the rigid tip section. The rigid tip section has openings connected to respective ends of a light guide fiber, an air/water tube, a forceps tube, and the like. Through the openings, the region of interest is illuminated, the objective window is washed or dried, and the region of interest is treated or a sample is taken using an appropriate tool.

It is important to shorten the rigid tip section in addition to reduction of its diameter because a longer rigid tip section increases physical stress on a patient and restricts bending of a flexible tube section in a narrow body cavity. To shorten the rigid tip section, it is necessary to make the imaging device, being a major component of the rigid tip section, as thin as possible. The length of the imaging device in an axial direction also needs to be shortened. For example, an imaging optical system for an endoscope disclosed in U.S. Pat. No. 4,674,844 (corresponding to Japanese Examined Patent Application Publication No. 6-48327) is designed on the premise that an image sensor is used. The imaging optical system allows principal rays to be incident obliquely on edges of an image plane. A field angle (2ω) is widened to approximately 100° to 118° while the thickness of the imaging optical system itself is reduced to 3.5-4.7 mm and the total length of the imaging optical system, between the front surface (first surface) of the imaging optical system and the image plane, is reduced to 4.2-5.5 mm.

In the wide angle imaging optical system, light rays before and after passing through the aperture stop are scattered. Hence, in the imaging optical system, the light rays move away from the optical axis at an incident surface proximate to an object and at an exit surface (last surface) proximate to the image plane. Because the outer diameter of the imaging optical system is determined in accordance with an outer diameter of the lens proximate to the object or the lens proximate to the image plane, it is required to reduce the diameters of these lenses to reduce the diameter of the imaging optical system. It is necessary to use the largest image sensor possible for the imaging device to be incorporated in an extremely limited space such as the distal end portion of the endoscope. The image size of the imaging optical system needs to be substantially the same as an effective screen size of the image sensor. To improve the image quality while the diameter of the imaging optical system is reduced, it is advantageous to enlarge the outer diameter of the imaging optical system to an extent not exceeding the image size.

In view of the above, the imaging optical system disclosed in the U.S. Pat. No. 4,674,844 is not suitable for current endoscopes that require reduction in diameter and in length, because the outer diameter is large relative to the maximum image height corresponding to the image size, and the lens thickness (the length of the lenses in the optical axis direction) of the entire optical system is long. The above-described requirements for size reduction also apply to the imaging devices incorporated in thin mobile information terminals (PDA: Personal Digital Assistants), typically, mobile phones.

SUMMARY OF THE INVENTION

An object of the present invention is to provide an imaging optical system with a short length between a front surface and an image plane relative to a required image size and with an outer diameter in a range appropriate for the image size, and to provide an imaging device having the imaging optical system and an image sensor.

An imaging optical system of the present invention comprises, in this order from an object side, a negative first lens group, a positive second lens group, a positive third lens group, and a negative fourth lens group. An aperture stop is provided between the second and third lens groups. The order of concave, convex, convex, and concave lens groups is symmetrical about the aperture stop. The imaging optical system satisfies expressions (1) to (5).

$$2.00 < TL/IH < 3.00 \quad (1)$$

$$0.37 < hF/IH < 0.5 \quad (2)$$

$$0.37 < hR/IH < 0.5 \quad (3)$$

$$3.5 < |f1/IH| < 4.5 \quad (4)$$

$$1.8 < \text{sum}/IH < 2.1 \quad (5)$$

"IH" represents a maximum image height. "TL" represents a total length of "sum" and a back focal length. The "sum" represents the lens thickness of the entire imaging optical system. "hF" represents an incident height of a principal ray, corresponding to the maximum image height "IH", at a surface proximate to the object side. "hR" represents an exit height of the principal ray at a surface proximate to an image plane. "f1" represents a focal length of the first lens group.

By satisfying the expressions (1) to (5), the total length of the imaging optical system between the front surface proximate to the object side and the image plane is shortened. The height of the principal ray incident on the first lens group proximate to the object side and the height of the principal ray exiting from the fourth lens group proximate to the image plane fall within appropriate ranges relative to the maximum image height and are approximately equal to each other. Thereby, an outer diameter of the imaging optical system is reduced. This is advantageous in correcting chromatic aberration. To correct various aberrations, it is preferable that the lower limit of the expression (1) is 2.211.

As a specific embodiment, it is preferable that the first lens group is a single lens with a concave surface facing the image plane, and the fourth lens group is a single lens with a concave surface facing the object side. It is preferable that at least one of the second lens group and the third lens group is a doublet made up of a positive lens element and a negative lens element attached together. Thereby, the chromatic aberration is corrected while other aberrations are suppressed. The present invention is effectively applied to an imaging device comprising the imaging optical system and an image sensor such as a back-illumination type CMOS image sensor or an organic CMOS image sensor. Photoelectric conversion efficiency of such image sensor does not decrease significantly even if an angle of incidence of the principal ray on an incident surface exceeds 30°. Particularly, the present invention is effective for the imaging device incorporated in a distal end portion of an endoscope for imaging a body cavity.

The outer diameter and the total length of the wide angle imaging optical system of the present invention are small even if the field angle exceeds 100°. Also, the imaging optical system corrects various aberrations including chromatic aberration, allowing production of sharp images. Thus, the imaging optical system is effectively used for the imaging device incorporated in a distal end portion of an endoscope or a mobile information terminal device.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
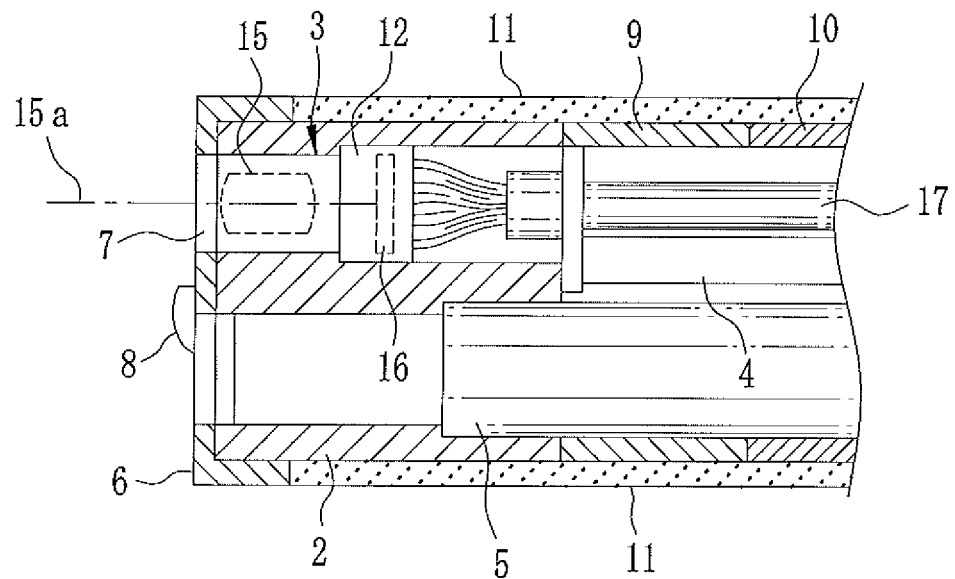
FIG. 1 is a cross-sectional view of a distal end portion, in which an imaging device of the present invention is incorporated, of an endoscope.

In FIG. 1, holes or passages are formed in an axial direction through a cylindrical rigid tip section 2 made from metal such as stainless steel. An end of an imaging device 3, an end of a light guide 4, and an end of a forceps pipe 5 are fixed to the holes, respectively. A cap 6 is fixed so as to cover an end face of the rigid tip section 2. The cap 6 is formed with openings that are connected to the respective holes of the rigid tip section 2. An opening 7 is a capture window that exposes a front face of the imaging device 3. An opening which exposes a front face of the light guide 4 is a lighting window. A nozzle 8 is connected to an opening in front of a water pipe. The nozzle 8 ejects cleaning water to the front face of the imaging device 3 to clean it.

A nodal ring structure 10 is connected to a rear end of the rigid tip section 2 through a coupling ring 9. Control force from a handling section of an endoscope is transmitted through a wire to the coupling ring 9, and, as is well known, the nodal ring structure 10 bends in accordance with the direction of the operation of the handling section (not shown). Thereby, the rigid tip section 2 is directed as desired. Outer circumferential surfaces of the rigid tip section 2, the coupling ring 9, and the nodal ring structure 10 are covered with a flexible waterproof cover 11.

The imaging device 3 is composed of a metal barrel body 12, an imaging optical system 15 and an image sensor 16. The imaging optical system 15 and the image sensor 16 are incorporated in the barrel body 12. The barrel body 12 is fixed to surround the holes formed through the rigid tip section 2. Signal lines from a coaxial cable 17 are connected to a connection terminal group exposed from the back of the barrel body 12. Each signal line is used for transmitting a drive signal for driving the image sensor 16 and an image signal obtained from the image sensor 16.

The imaging device 3 is a direct-view type in which an incident surface of the image sensor 16 is vertical to an optical axis 15a of the imaging optical system 15. Light rays from a last surface of the imaging optical system 15 are incident on an image plane (that is, the incident surface of the image sensor 16) at various angles. An angle of incidence of a principal ray on an edge of the image plane is larger than an angle of incidence of the principal ray at the center of the image plane. This applies the same for a so-called side-view type imaging device in which the light rays from the last surface of the imaging optical system 15 are refracted by a prism and then incident on the image sensor 16. The image sensor 16 may be a CCD type or a CMOS type. In view of power consumption and manufacturing cost, the CMOS image sensor 16 is widely used.

Figure 2A:
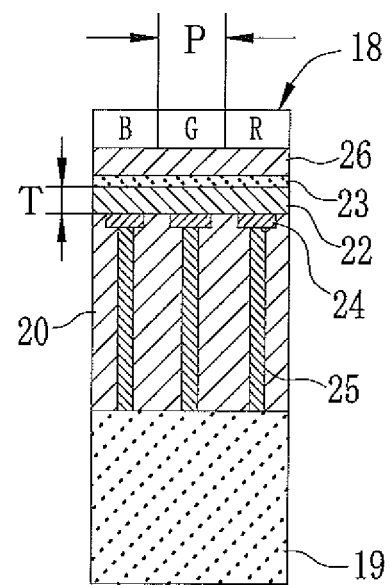
FIG. 2A is a schematic cross-sectional view of an organic CMOS image sensor.
Figure 2B:
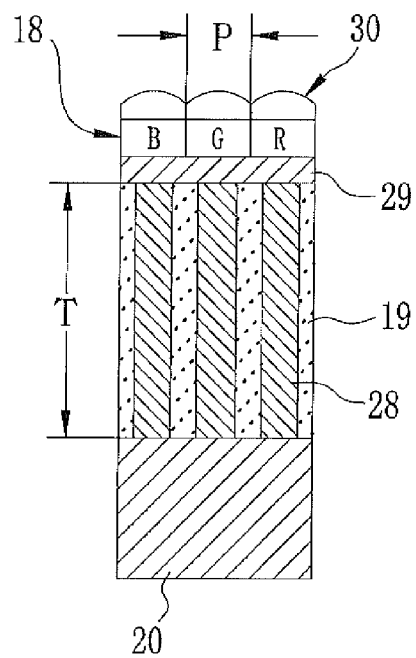
FIG. 2B is a schematic cross-sectional view of a back-illumination type CMOS image sensor.
Figure 2C:
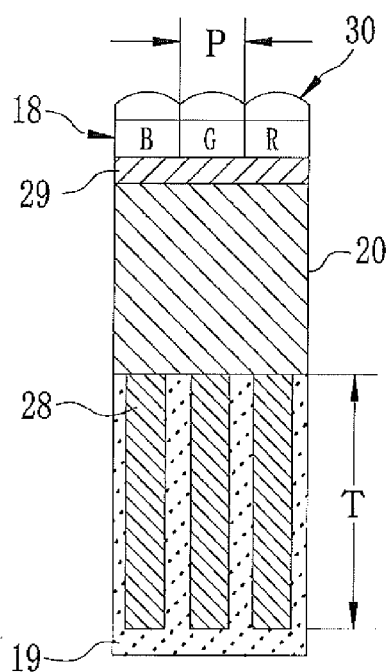
FIG. 2C is a schematic diagram illustrating an internal structure of a front-illumination type CMOS image sensor.

In this embodiment, a CMOS image sensor is used as the image sensor 16. The CMOS image sensor (hereinafter referred to as the organic CMOS sensor) performs photoelectric conversion using an organic photoelectric conversion film. The organic CMOS sensor having a structure schematically shown in FIG. 2A is disclosed in, for example, "FUJIFILM RESEARCH & DEVELOPMENT" (No. 55-2010). For comparison, a structure of a back-illumination type CMOS image sensor is schematically shown in FIG. 2B. A structure of a front-illumination type CMOS image sensor is schematically shown in FIG. 2C. Like numerals refer to like parts in FIGS. 2A to 2C.

A micro color filter layer 18 is composed of blue (B light) transmission filters, green (G light) transmission filters, and red (R light) transmission filters arranged in a predetermined pattern such as a Bayer arrangement. "P" in the drawing corresponds to a pixel. The organic CMOS sensor comprises a semiconductor substrate 19 provided with a read circuit (not shown), a circuit layer 20, a pixel electrode 24, an organic photoelectric conversion film 22, and a transparent opposite electrode 23 (in this order from the bottom). The circuit layer includes networks such as a switching circuit and an amplification circuit. The switching circuit is used to read an image signal, obtained from each pixel, through the pixel electrode 24. These circuits are electrically connected to each other through a connector 25 provided in the circuit layer 20. A transparent protection layer 26 is formed over the opposite electrode 23. A micro color filter layer 18 covers the protection layer 26.

In the back-illumination type CMOS image sensor shown in FIG. 2B, photoelectric conversion sections 28, corresponding to the respective pixels, are provided in the semiconductor substrate 19. Each photoelectric conversion section 28 is made from a silicon photodiode. In the back-illumination type CMOS image sensor, a passivation film 29 and the micro color filter layer 18 are layered over the semiconductor substrate 19. A microlens array 30 is placed over the micro color filter layer 18 such that each pixel is covered with a microlens. The circuit layer 20 including the switching circuit that reads out the image signal from each pixel is provided below the photoelectric conversion section 28 (namely, on the opposite side of the light incident surface).

In the front-illumination type CMOS image sensor shown in FIG. 2C, the photoelectric conversion section 28 made from the silicon photodiode is provided in the semiconductor substrate 19. The circuit layer 20, the passivation film 29, and the micro color filter layer 18 are provided over the photoelectric conversion section 28. The microlens array 30 is placed over the micro color filter layer 18 such that each pixel is covered with a microlens.

As shown in FIGS. 2A and 2B, in the organic CMOS sensor and the back-illumination type CMOS image sensor, a top surface of the organic photoelectric conversion film 22 or the photoelectric conversion section 28, being a light receiving surface for the photoelectric conversion, is located above the circuit layer 20. Hence, the light receiving surface is provided close to an outermost surface, being the light incident surface. In the front-illumination type CMOS image sensor shown in FIG. 2C, the top surface of the photoelectric conversion section 28, being the light receiving surface, is located below the circuit layer 20. In the organic CMOS sensor, the thickness of the organic photoelectric conversion film, which functions as the photoelectric conversion section, is 0.5 µm. In the back-illumination type CMOS image sensor and the front-illumination type CMOS image sensor, the thickness of the photoelectric conversion section made from the silicon photodiode is in the order of 5 µm in the depth direction.

In the organic CMOS sensor and the back-illumination type CMOS image sensor, the loss of the incident light flux is reduced by placing the light receiving surface of the photoelectric conversion section above the circuit layer 20. Thereby, the sensitivity of each of the organic CMOS sensor and the back-illumination type CMOS image sensor increases as compared with that of the front-illumination type CMOS image sensor. In the organic CMOS sensor and the back-illumination type CMOS image sensor, vignetting of the incident light by the circuit layer 20 before the incident light reaches the light receiving surface is prevented. Hence, sensitivity degradation caused by the light rays incident at a certain angle is prevented. When a thickness T in the depth direction of the organic photoelectric conversion film 22 or the photoelectric conversion section 28 is reduced, leakage of the incident light, transmitted vertically and obliquely through the micro color filter layer 18, to the photoelectric conversion section 28 of an adjacent pixel is prevented. Thus, the occurrence of color mixing is reduced.

To prevent the color mixing, the back-illumination type CMOS sensor shown in FIG. 2B requires the microlens array 30 that allows oblique light to be incident as vertically as possible on the micro color filter layer 18. On the other hand, the color mixing is not likely to occur in the organic CMOS sensor with no microlens array 30 shown in FIG. 2A, because the top surface of the organic photoelectric conversion film 22, being the light receiving surface for the photoelectric conversion, is located close to the micro color filter layer 18.

Figure 3:
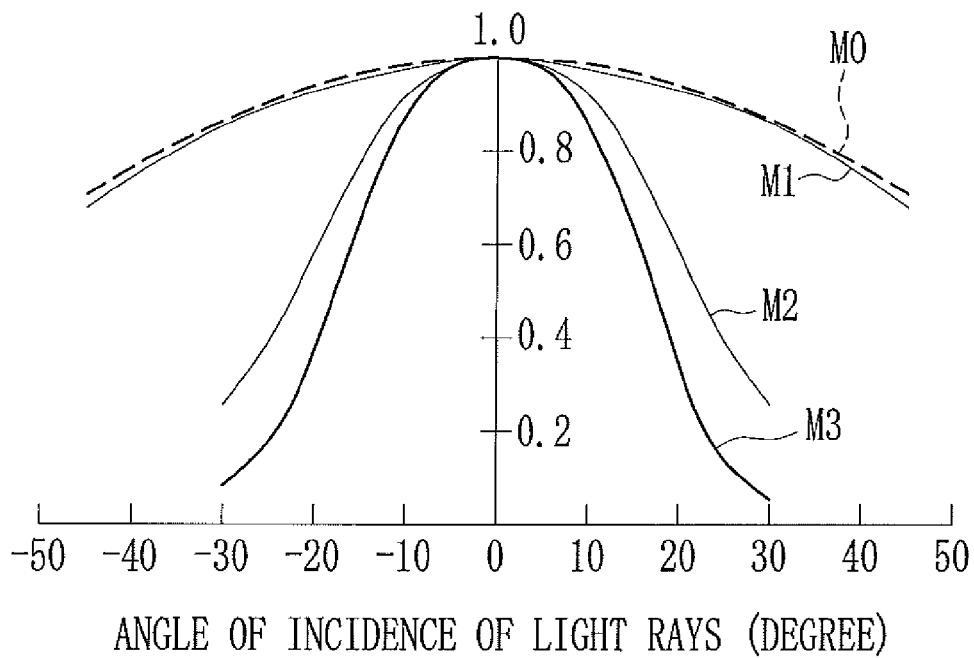
FIG. 3 is a characteristic diagram illustrating photoelectric conversion efficiency of the image sensors.

In the back-illumination type and the front-illumination type CMOS image sensors shown in FIGS. 2B and 2C, percentage of the light rays incident on the photoelectric conversion section 28 of the pixel decreases drastically when the light rays are incident at an angle greater than or equal to 30° relative to a normal to the micro color filter layer 18 even if the appropriate microlens array 30 is used. FIG. 3 shows the decrease of the incident light using relative sensitivity. In FIG. 3, the angle of incidence of 0° corresponds to vertical incidence. In FIG. 3, "M3" denotes sensitivity characteristics of a conventional front-illumination type CMOS image sensor. The sensitivity is reduced to in the order of 35% relative to that of the vertical incidence when the angle of incidence of the light rays is in the order of ±20°. The angle of incidence of ±30° is approximately the limit.

"M2" denotes sensitivity characteristics of the back-illumination type CMOS image sensor. Although the sensitivity degrades when the angle of incidence of the light rays is in the order of ±20°, as compared with that of the vertical incidence, the sensitivity in the order of 50% is maintained. Even at the angle of incidence of ±30°, the sensitivity in the order of 25% is maintained, which is superior to that of the front-illumination type CMOS image sensor. The organic CMOS sensor has sensitivity characteristics represented by "M1", which is as high as a cosine curve M0, being a theoretical limit. The organic CMOS sensor has sensitivity sufficient for practical use even at around ±45°. This is because the thin organic photoelectric conversion film is located close to the light incident surface as described above.

As described above, the sensitivity characteristics of the organic CMOS sensor are significantly superior to those of the back-illumination type CMOS image sensor. The sensitivity characteristics of the organic CMOS sensor are overwhelmingly superior to those of the front-illumination type CMOS image sensor. Nevertheless, it is sufficient for practical use when the sensitivity to the light rays at an angle of incidence of ±30° is greater than 20% relative to that of the vertical incidence. Hence, it is possible to use the back-illumination type CMOS image sensor as the image sensor 16 of the imaging device 3 of the present invention. By using such image sensor, restrictions on the maximum angle of incidence of the principal rays on the image plane are reduced. This facilitates designing the imaging optical system 15 and is advantageous in narrowing the optical system, reducing a total length of the optical system, and maintaining high imaging performance with low aberrations, within ranges suitable for the image size.

Because the conventional CMOS image sensor is sensitive to the infrared region, the conventional CMOS image sensor normally incorporates an infrared cut filter in an optical system. The infrared cut filter comprising a common multi-layer film has spectral transmission characteristics depicted by T0 in FIG. 4, for example. The half the maximum transmittance, relative to the vertically incident light, is set to approximately 650 nm. Wavelength shift is caused by light rays obliquely incident on the infrared cut filter. The transmission characteristics vary as depicted by T1 at 20° incidence, T2 at 30° incidence, and T3 at 40° incidence. This results in color shading. The color shading causes a color of an image corresponding to a center of a screen, on which the light rays are incident at small angles, different from a color of the image corresponding to corners of the screen, on which the light rays are incident at large angles. To prevent the color shading, it is necessary for the conventional CMOS image sensor to reduce the maximum angle of incidence of the principal rays on corners of the image plane to 25°-30°.

Figure 4:
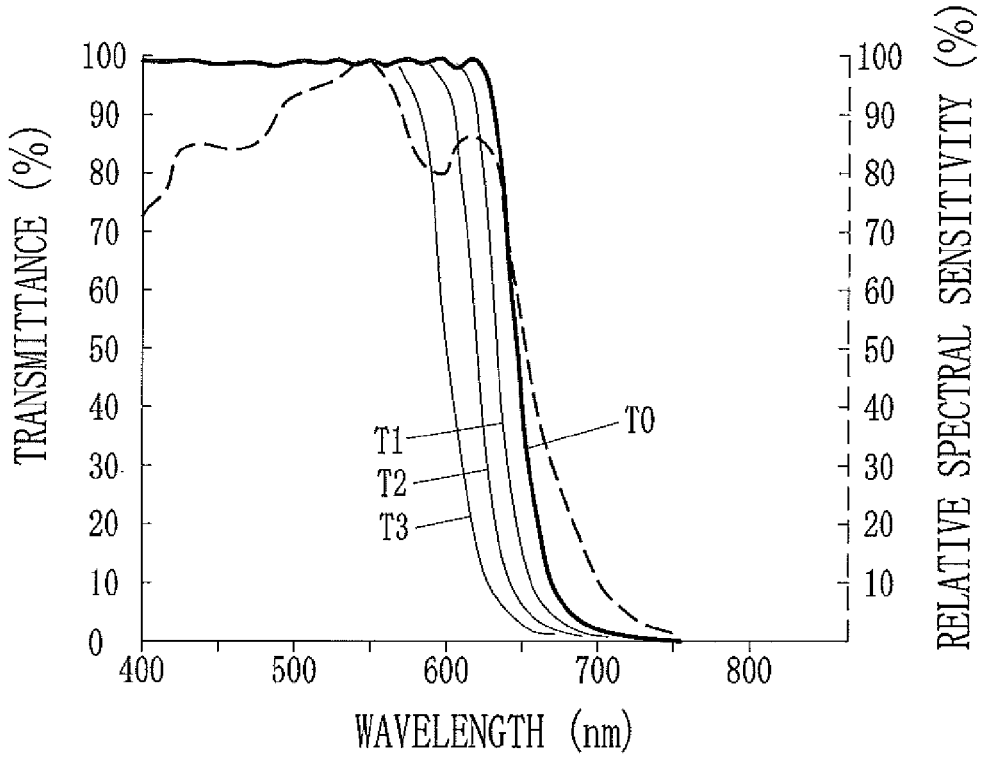
FIG. 4 is a graph representing spectral transmission characteristics of an infrared cut filter.

The sensitivity of the organic CMOS image sensor decreases significantly in the infrared region as depicted with a broken line in FIG. 4. Hence, the organic CMOS image sensor can be used without incorporating the infrared cut filter in the optical system. With no infrared cut filter, the color shading, caused by a difference in angles of incidence of light rays on the image plane, is prevented and the manufacturing cost is reduced. Thus, it is optimum to use the organic CMOS sensor as the image sensor 16 of the imaging device 3.

The imaging optical system 15 and the image sensor 16 are incorporated in the barrel body 12, and fitted into and fixed to the hole provided through the rigid tip section 2. The image sensor 16 is incorporated in the barrel body 12 such that the light incident surface of the image sensor 16 is coincident with the image plane of the imaging optical system 15. The image sensor 16 images a subject image formed by the imaging optical system 15. Note that a maximum image height (the distance from the optical axis 15a) of the subject image effectively formed by the imaging optical system 15 is 1.5 mm.

An outer diameter of the imaging optical system 15 incorporated in the barrel body 12 is within an outline of the image sensor 16 so as to make the rigid tip section 2 compact. The lens construction is determined to make the total lens thickness or the distance between the front surface (first surface) of the imaging optical system 15 and the image plane short while deterioration of the image quality is prevented. Basically, it is preferable to arrange a negative first lens group, a positive second lens group, a positive third lens group, and a negative fourth lens group in this order from an object side.

The entire optical system is downsized by satisfying the following expressions (1) to (3) where "IH" represents the maximum image height on the image plane, "TL" represents the total length of the optical system that is the sum of the thicknesses of the lenses of the entire optical system and a back focal length between the last surface and the image plane, "hF" represents an incident height, of the principal ray corresponding to the maximum image height IH, from the optical axis 15a at the surface proximate to the object side, and "hR" represents an exit height, of the principal ray corresponding to the maximum image height IH, from the optical axis 15a at the surface proximate to the image plane.

$$2.00 < TL/IH < 3.00 \quad (1)$$

$$0.37 < hF/IH < 0.5 \quad (2)$$

$$0.37 < hR/IH < 0.5 \quad (3)$$

The expression (1) represents an appropriate range of the total length TL between the incident surface of the front lens (the lens proximate to the object side) and the image plane. The expression (2) represents an appropriate range of the incident height hF, of the principal ray incident on the front lens and directed to a position of the maximum image height IH on the image plane, from the optical axis 15a at the front lens. Hereinafter, the position of the maximum image height IH is referred to as the maximum image height position. The expression (3) represents an appropriate range of the exit height hR, of the principal ray exiting from the last lens and directed to the maximum image height position on the image plane, from the optical axis 15a at the last lens. Each of the ranges are standardized with the maximum image height on the image plane. Namely, the expression (1) represents an appropriate range of the total length TL of the imaging optical system when the maximum image height is 1 mm. The expression (2) represents an appropriate range of the incident height hF of the principal ray incident on the imaging optical system and directed to the maximum image height position, when the image with the maximum image height IH of 1 mm is formed. The expression (3) represents an appropriate range of the exit height hR of the principal ray exiting from the imaging optical system and directed to the maximum image height position, when the image with the maximum image height IH of 1 mm is formed.

When the value TL/IH exceeds the upper limit of the expression (1), the total length of the optical system cannot be reduced sufficiently. When the value TL/IH is less than the lower limit, correction of various aberrations is difficult. The expressions (2) and (3) correspond to factors which restrict the outer diameters of the first and fourth lens groups. When the values (hF/IH, hR/IH) exceed the upper limits, the outer diameters become too large relative to the maximum image height IH, which is disadvantageous for downsizing. When the values (hF/IH, hR/IH) are less than the lower limits, the outer diameters become too small so that the optical surfaces require high surface accuracy. As a result, manufacturing cost of each lens increases.

It is effective to provide an aperture stop between the second lens group and the third lens group of the imaging optical system 3 so as to achieve symmetrical power distribution about the aperture stop and facilitate correction of chromatic aberration. It is effective to satisfy an expression (4) where f1 represents the focal length of the first lens group.

$$3.5 < |f1/IH| < 4.5 \quad (4)$$

When the value (|f1/IH|) exceeds the upper limit of the expression (4), the negative power of the first lens group becomes too small, so that downsizing is difficult when the wide angle is achieved. When the value (|f1/IH|) is less than the lower limit of the expression (4), the negative power becomes too large, so that the correction of aberration, particularly, correction of a tilt of the image plane is difficult.

It is effective to satisfy an expression (5) where "sum" denotes the thickness of the lenses between the surface, proximate to the object side, of the first lens group and the surface, proximate to the image plane, of the fourth lens group.

$$1.8 < sum/IH < 2.1 \quad (5)$$

When the value "sum/IH" exceeds the upper limit of the expression (5), the lens thickness becomes too large so that the total length of the optical system cannot be reduced sufficiently. When the value "sum/IH" is less than the lower limit, correction of astigmatism is difficult. In consideration of the correction of various aberrations including the chromatic aberration, it is preferable that at least one of the second and third lens groups of positive power is composed of a doublet made up a positive lens element and a negative lens element attached together. The aperture stop is provided between the second and third lens groups.

Hereinafter, referring to data (optical system data) of the optical system, lens construction diagrams, and aberration diagrams, examples 1 to 10 of the imaging optical systems 15 are described. In the drawings showing the lens constructions, "G1" denotes the first lens group. "G2" denotes the second lens group. "G3" denotes the third lens group. "G4" denotes the fourth lens group. The first to fourth lens groups G1 to G4 are arranged in this order from the object side. "S" denotes the aperture stop. "IP" denotes the image plane. In each example, the imaging optical system 15 has concave-convex-convex-concave power distribution, from the first lens group. The aperture stop S is provided between the second and third lens groups. The order of the concave and convex lens groups is symmetrical about the aperture stop. In the examples in which the second or third lens group is composed of the doublet, "G2$a$" and "G2$b$", or "G3$a$" and "G3$b$" denote the respective single lens elements attached together. Note that each of the first lens group G1 and the fourth lens group G4 is composed of a single lens. Alternatively, at least one of the first and fourth lens groups G1 and G4 may be composed of a doublet.

For each surface number assigned from the object side, the optical system data shows a curvature radius "r" and a distance "d" between the surfaces each in the unit of mm. The values other than field angles (unit: degree) and exit angles (unit: degree) are also shown in the unit of mm. In each spherical aberration diagram, "F", "d", and "C" denote aberration characteristics corresponding to wavelengths of spectral lines F (486.1 nm), d (587.6 nm), and C (656.3 nm), respectively. In each astigmatism diagram, "s" and "t" denote sagittal and tangential aberration characteristics, respectively. Note that the back length BL denotes the distance between the last surface of the lens and the image plane when the object distance is infinite.

Generally, the object distance of the optical system for the endoscope is short as compared with that of a common optical system. The image sensor (the image plane) is moved toward the back such that the optimum focal position of the optical system corresponds to the predetermined object distance suitable for observation using the endoscope. Namely, the optical system for the endoscope is used with the back length longer than that for the infinite object distance. Shorter the object distance, the larger the amount of shift of the image plane toward the back. The approximate shift amount is obtained by dividing the square of the focal length by the object distance. The aberration diagram in each example is obtained with the objective distance of 10 mm.

For each of the total length TL of the optical system, the incident height hF, the exit height hR, the absolute value |f1| of the focal length f1 of the first lens group, and the lens thickness "sum" between the front surface of the first lens group and the last surface of the fourth lens group, a value standardized with the maximum image height IH is also shown with an asterisk "*" prefixed, for example "*TL". The incident height hF indicates the height of the principal ray, to be incident on the maximum image height position on the image plane, at a position of incidence on the incident surface of the first lens group from the optical axis. The exit height hR indicates the height of the principal ray, to be incident on the maximum image height position on the image plane, at an exit position on the exit surface of the fourth lens group from the optical axis.

EXAMPLE 1

Figure 5:
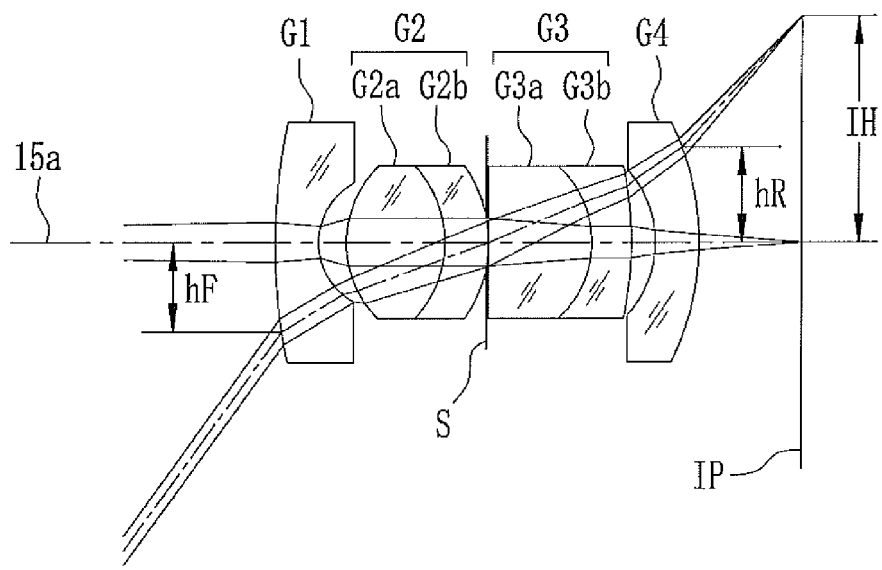
FIG. 5 is a lens construction diagram of an optical system of an example 1 of the present invention.

The imaging optical system 15 has a lens construction shown in FIG. 5. The optical system data is shown in table 1. The incident height [hF] at the front surface, the exit height [hR] on the last surface, and the maximum image height IH shown in the table 1 indicate the respective heights from the optical axis 15$a$ as illustrated in FIG. 5 by way of example.

TABLE 1

| Surface No. | r | d | nd | vd | | |
|---|---|---|---|---|---|---|
| 1 | 4.000 | 0.300 | 1.88300 | 40.80 | f1 | −0.621 |
| 2 | 0.465 | 0.170 | | | f2 | 0.641 |
| 3 | 0.667 | 0.680 | 1.83481 | 42.71 | f3 | 3.122 |
| 4 | −0.667 | 0.260 | 1.80518 | 25.42 | f4 | −1.404 |
| 5 | −1.000 | 0.000 | | | fF | 0.989 |
| 6 | aperture stop | 0.030 | | | D1 | 1.410 |
| | | | | | fR | −2.677 |
| 7 | 0.000 | 0.680 | 1.83481 | 42.71 | D2 | 1.440 |
| 8 | −0.667 | 0.260 | 1.80518 | 25.42 | | |
| 9 | −2.900 | 0.170 | | | | |
| 10 | −0.675 | 0.300 | 1.88300 | 40.80 | | |
| 11 | −1.790 | | | | | |

| | |
|---|---|
| focal length [f] | 1.257 |
| back length [BL] | 0.501 |
| lens thickness [sum] | 2.850 |
| total length [TL] | 3.351 |
| field angle [2ω](°) | 108.5 |
| exit angle [2δ](°) | 95.5 |
| incident height [hF] | 0.598 |
| exit height [hR] | 0.635 |
| maximum image height [IH] | 1.500 |

| value standardized with image height | |
|---|---|
| *TL | 2.234 |
| *hF | 0.399 |
| *hR | 0.423 |
| *|f1| | 0.414 |
| *sum | 1.900 |

In tables 1 to 10, "f1" denotes the focal length of the first lens group, "f2" denotes the focal length of the second lens group, "f3" denotes the focal length of the third lens group, and "f4" denotes the focal length of the fourth lens group. "fF" denotes the focal length of a front lens group. "D1" denotes the distance between the front surface and the aperture stop. "fR" denotes the focal length of a rear lens group. "D2" denotes the distance between the aperture stop and the last surface.

In the optical system of the example 1, the second lens group G2 is composed of a doublet made up of a positive lens element G1$a$ and a negative lens element G2$b$ arranged in this order from the object side. The third lens group G3 is composed of a doublet made up of a positive lens element G3$a$ and a negative lens element G3$b$ arranged in this order from the object side. In total, the optical system is composed of six lenses in four groups. The total length TL between the front surface of the first lens group G1 and the image plane IP is 3.351 mm, the lens thickness "sum" is 2.850 mm, the incident height hF at the front surface is 0.598 mm, and the exit height hR at the last surface is 0.635 mm, when the maximum image height IH is 1.500 mm. Hence, it is sufficient that the calculated outer diameter of each of the first and fourth lens groups G1 and G4, which determines the outer diameter of the imaging optical system 15, be 1.5 mm.

Thus, the outer diameter of the imaging optical system 15 is sufficiently small relative to the screen size (in the order of 3×3 mm) of the image sensor 16. The imaging optical system 15 is suitably used for the wide-angle imaging device 3 incorporated in the rigid tip section 2 of the endoscope even if the actual diameter of the imaging optical system 15 becomes larger with the use of a flange extending outside of the effective diameter, when suitability of the imaging optical system 15 to be incorporated into the barrel body 12 and suitability for manufacture of each of the lens groups including the second and third lens groups G2 and G3 are taken into consideration.

Figure 6:
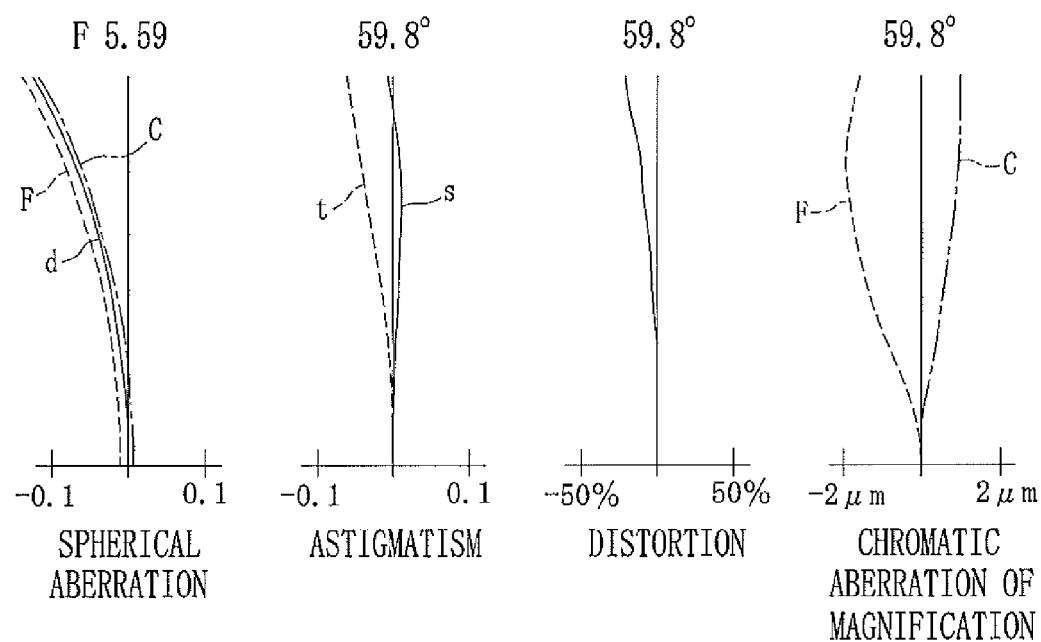
FIG. 6 is an aberration diagram of the example 1.

The value "*TL" obtained by standardizing the total length TL with the maximum image height IH, the value "*hF" obtained by standardizing the incident height hF with the maximum image height IH, the value "*hR" obtained by standardizing the exit height hR with the maximum image height IH, and the value "sum" obtained by standardizing the lens thickness "sum" with the maximum image height IH satisfy the conditions specified by the expressions (1), (2), (3), and (5), respectively. The value "*|f1|", obtained by standardizing the absolute value |f1| of the focal length f1 of the first lens group G1 with the maximum image height IH, is within the range defined by the expression (4). Hence, the imaging optical system ensures the field angle 2ω of 137° while correcting various aberrations as shown in FIG. 6. The imaging optical system is widely used for various imaging devices which require wide field angles in addition to endoscopes.

EXAMPLE 2

Figure 7:
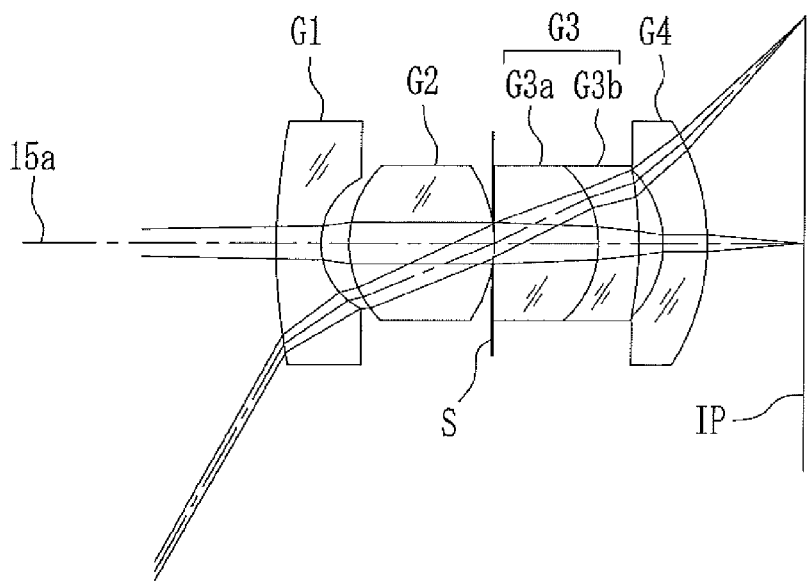
FIG. 7 is a lens construction diagram illustrating an optical system of an example 2 of the present invention.
Figure 8:
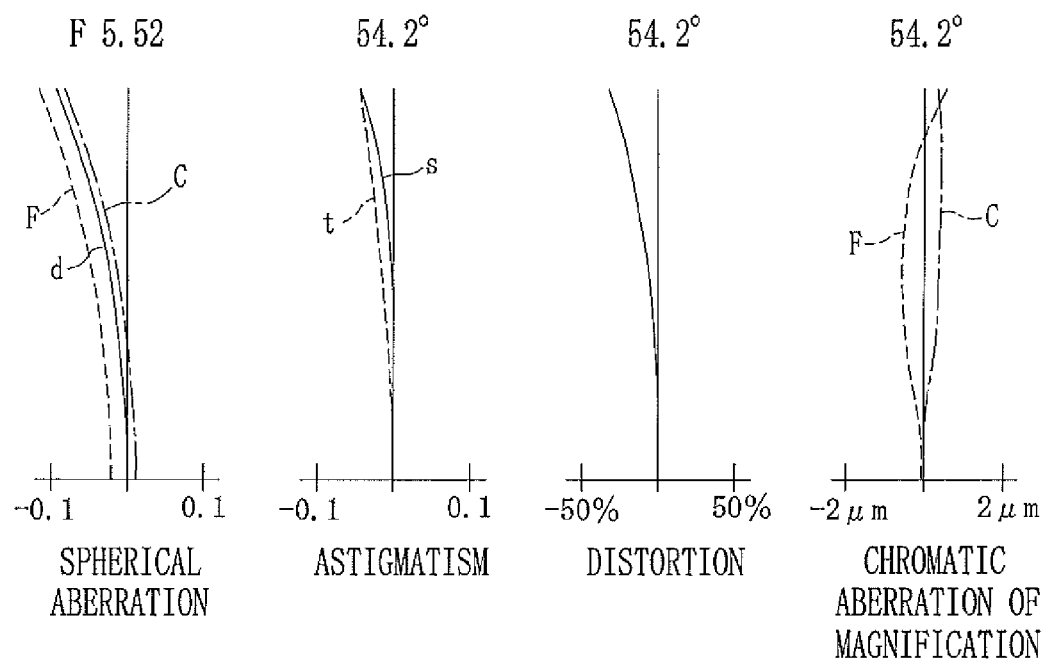
FIG. 8 is an aberration diagram of the example 2.

The imaging optical system 15 has a lens construction composed of five lenses in four groups as shown in FIG. 7. The optical system data is shown in table 2. The aberration characteristics are shown in FIG. 8.

TABLE 2

| Surface No. | r | d | nd | νd | | |
|---|---|---|---|---|---|---|
| 1 | 3.850 | 0.300 | 1.88300 | 40.80 | f1 | −0.634 |
| 2 | 0.471 | 0.170 | | | f2 | 0.645 |
| 3 | 0.667 | 0.940 | 1.83481 | 42.71 | f3 | 3.212 |
| 4 | −1.000 | 0.000 | | | f4 | −1.805 |
| 5 | aperture stop | 0.030 | | | fF | 0.992 |
| | | | | | D1 | 1.410 |
| 6 | 0.000 | 0.680 | 1.83481 | 42.71 | fR | −4.151 |
| 7 | −0.667 | 0.260 | 1.80518 | 25.42 | D2 | 1.440 |
| 8 | −2.997 | 0.170 | | | | |
| 9 | −0.672 | 0.300 | 1.88300 | 40.80 | | |
| 10 | −1.405 | | | | | |

| | |
|---|---|
| focal length [f] | 1.191 |
| back length [BL] | 0.466 |
| lens thickness [sum] | 2.85 |
| total length [TL] | 3.316 |
| field angle [2ω](°) | 119.6 |
| exit angle [2δ](°) | 93.3 |
| incident height [hF] | 0.665 |
| exit height [hR] | 0.669 |
| maximum image height [IH] | 1.500 |

TABLE 2-continued

| | value standardized with image height |
|---|---|
| *TL | 2.211 |
| *hF | 0.443 |
| *hR | 0.446 |
| *|f1| | 0.423 |
| *sum | 1.900 |

The optical system has a lens construction composed of five lenses in four groups. The third lens group G3 is composed of a doublet made up of a positive lens element G3a and a negative lens element G3b. The total length TL of the optical system is 3.316 mm, the lens thickness "sum" is 2.85 mm, the incident height hF is 0.665 mm, the exit height hR is 0.669 mm, when the maximum image height IH is 1.5 mm. Hence, the total length and the outer diameter fall within appropriate ranges in a manner similar to the example 1. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "|f1|" obtained by standardizing the absolute value |f1| of the focal length f1 of the first lens group G1 with the maximum image height IH, and "*sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 3

Figure 9:
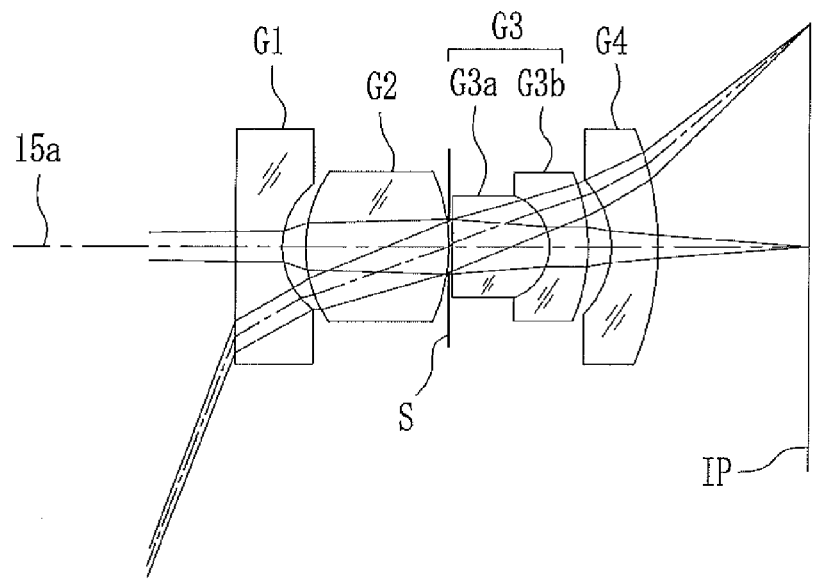
FIG. 9 is a lens construction diagram illustrating an optical system of an example 3 of the present invention.
Figure 10:
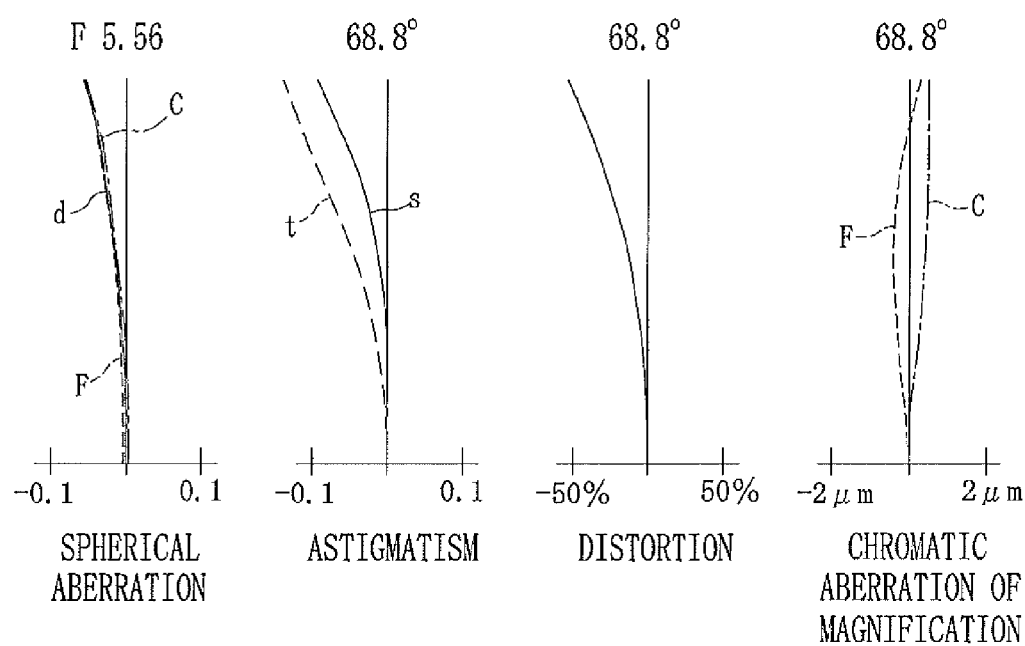
FIG. 10 is an aberration diagram of the example 3.

The imaging optical system 15 has a lens construction composed of five lenses in four groups as shown in FIG. 9. The optical system data is shown in table 3. The aberration characteristics are shown in FIG. 10.

TABLE 3

| Surface No. | r | d | nd | νd | | |
|---|---|---|---|---|---|---|
| 1 | 0.000 | 0.300 | 1.88300 | 40.80 | f1 | −0.593 |
| 2 | 0.524 | 0.180 | | | f2 | 0.785 |
| 3 | 0.893 | 0.950 | 1.83481 | 42.71 | f3 | 1.117 |
| 4 | −1.272 | 0.000 | | | f4 | −1.063 |
| 5 | aperture stop | 0.030 | | | fF | 1.827 |
| | | | | | D1 | 1.430 |
| 6 | 4.425 | 0.680 | 1.83481 | 42.71 | fR | 7.552 |
| 7 | −0.375 | 0.260 | 1.80518 | 25.42 | D2 | 1.430 |
| 8 | −1.135 | 0.160 | | | | |
| 9 | −0.613 | 0.300 | 1.88300 | 40.80 | | |
| 10 | −2.173 | | | | | |

| | |
|---|---|
| focal length [f] | 1.209 |
| back length [BL] | 0.88 |
| lens thickness [sum] | 2.86 |
| total length [TL] | 3.74 |
| field angle [2ω](°) | 137.6 |
| exit angle [2δ](°) | 81.3 |
| incident height [hF] | 0.597 |
| exit height [hR] | 0.553 |
| maximum image height [IH] | 1.500 |

TABLE 3-continued

| | value standardized with image height |
|---|---|
| *TL | 2.493 |
| *hF | 0.398 |
| *hR | 0.369 |
| *|f1| | 0.395 |
| *sum | 1.907 |

Similar to the example 2, the optical system has a lens construction composed of five lenses in four groups. The third lens group G3 is composed of a doublet made up of a positive lens element G3a and a negative lens element G3b. The total length TL of the optical system is 3.74 mm, the lens thickness "sum" is 2.86 mm, the incident height hF is 0.597 mm, the exit height hR is 0.553 mm, when the maximum image height IH is 1.5 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "*|f1|" obtained by standardizing the absolute value |f1| of the focal length f1 of the first lens group G1 with the maximum image height IH, and "*sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 4

Figure 11:
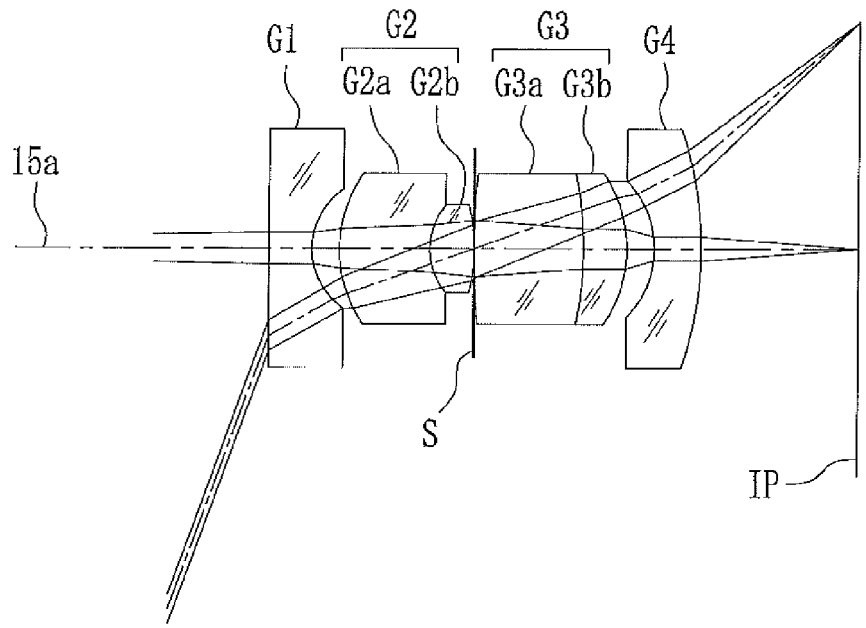
FIG. 11 is a lens construction diagram of an optical system of an example 4 of the present invention.
Figure 12:
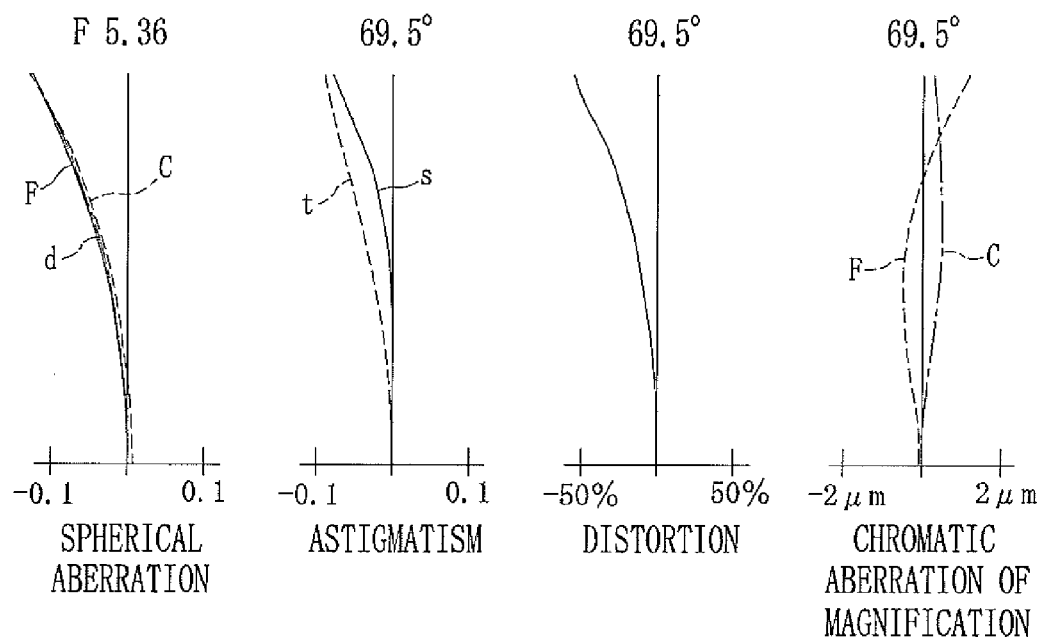
FIG. 12 is an aberration diagram of the example 4.

The imaging optical system 15 has a lens construction composed of six lenses in four groups as shown in FIG. 11. The optical system data is shown in table 4. The aberration characteristics are shown in FIG. 12.

TABLE 4

| Surface No. | r | d | nd | vd | | |
|---|---|---|---|---|---|---|
| 1 | 0.000 | 0.280 | 1.88300 | 40.80 | f1 | −0.579 |
| 2 | 0.511 | 0.180 | | | f2 | 0.751 |
| 3 | 0.923 | 0.600 | 1.80518 | 25.42 | f3 | 1.059 |
| 4 | 0.480 | 0.300 | 1.83481 | 42.71 | f4 | −0.975 |
| 5 | −1.124 | 0.000 | | | fF | 1.457 |
| 6 | aperture stop | 0.030 | | | D1 | 1.360 |
| | | | | | fR | 20.834 |
| 7 | 0.000 | 0.700 | 1.83481 | 42.71 | D2 | 1.510 |
| 8 | −3.232 | 0.300 | 1.80518 | 25.42 | | |
| 9 | −0.860 | 0.180 | | | | |
| 10 | −0.655 | 0.300 | 1.92286 | 18.90 | | |
| 11 | −2.936 | | | | | |

| | |
|---|---|
| focal length [f] | 1.194 |
| back length [BL] | 0.918 |
| lens thickness [sum] | 2.87 |
| total length [TL] | 3.788 |
| field angle [2ω](°) | 139.1 |
| exit angle [2δ](°) | 80.1 |
| incident height [hF] | 0.569 |
| exit height [hR] | 0.561 |
| maximum image height [IH] | 1.500 |

TABLE 4-continued

| | value standardized with image height |
|---|---|
| *TL | 2.525 |
| *hF | 0.379 |
| *hR | 0.374 |
| *|f1| | 0.386 |
| *sum | 1.913 |

The optical system has a lens construction composed of six lenses in four groups. The second lens group G2 is composed of a doublet made up of a negative lens element G2a and a positive lens element G2b. The third lens group G3 is composed of a doublet made up of a positive lens element G3a and a positive lens element G3b. The total length TL of the optical system is 3.788 mm, the lens thickness "sum" is 2.87 mm, the incident height hF is 0.569 mm, the exit height hR is 0.561 mm, when the maximum image height IH is 1.5 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "|f1|" obtained by standardizing the absolute value |f1| of the focal length f1 of the first lens group G1 with the maximum image height IH, and "sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 5

Figure 13:
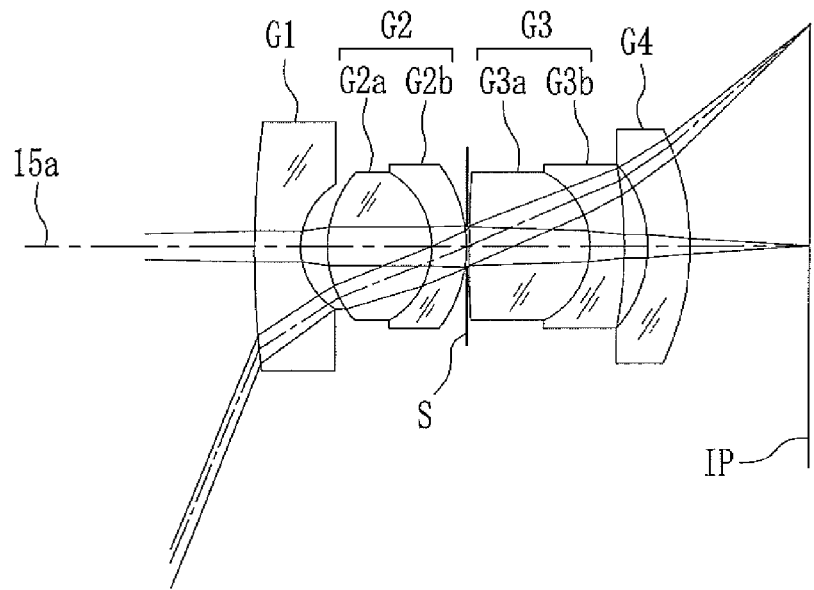
FIG. 13 is a lens construction diagram of an optical system of an example 5 of the present invention.
Figure 14:
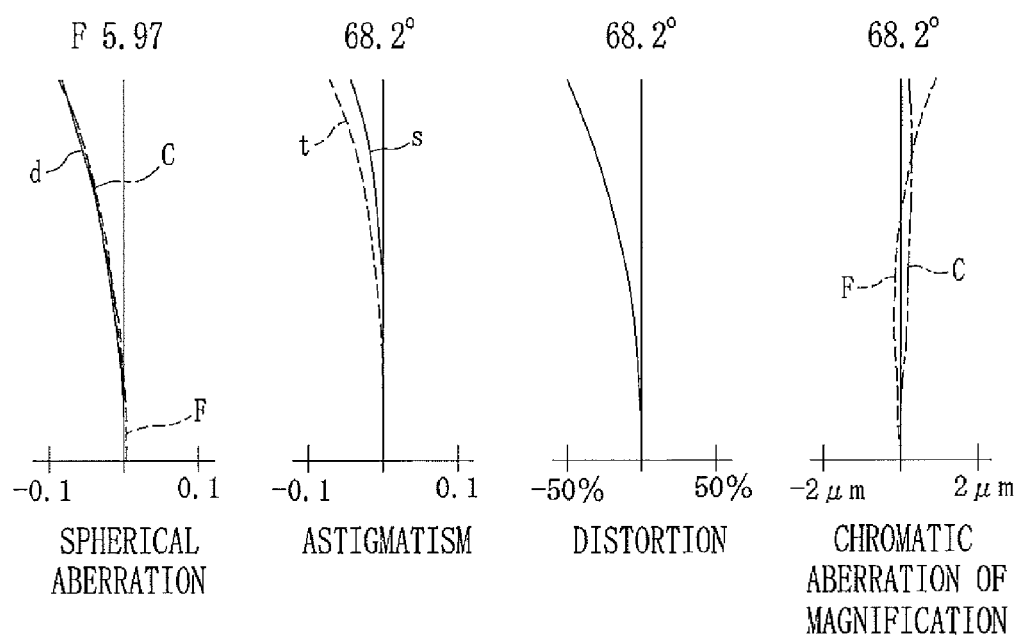
FIG. 14 is an aberration diagram of the example 5.

The imaging optical system 15 has a lens construction composed of six lenses in four groups as shown in FIG. 13. The optical system data is shown in table 5. The aberration characteristics are shown in FIG. 14.

TABLE 5

| Surface No. | r | d | nd | vd | | |
|---|---|---|---|---|---|---|
| 1 | 6.032 | 0.300 | 1.88300 | 40.80 | f1 | −0.602 |
| 2 | 0.477 | 0.195 | | | f2 | 0.692 |
| 3 | 0.741 | 0.702 | 1.80610 | 40.92 | f3 | 5.095 |
| 4 | −0.597 | 0.251 | 1.84666 | 23.78 | f4 | −3.237 |
| 5 | −0.930 | 0.000 | | | fF | 1.029 |
| 6 | aperture stop | 0.030 | | | D1 | 1.448 |
| | | | | | fR | −8.265 |
| 7 | 133.500 | 0.800 | 1.75500 | 52.32 | D2 | 1.530 |
| 8 | −0.553 | 0.250 | 1.84666 | 23.78 | | |
| 9 | −2.424 | 0.150 | | | | |
| 10 | −0.802 | 0.300 | 1.51742 | 52.43 | | |
| 11 | −1.735 | | | | | |

| | |
|---|---|
| focal length [f] | 1.19 |
| back length [BL] | 0.66 |
| lens thickness [sum] | 2.978 |
| total length [TL] | 3.638 |
| field angle [2ω](°) | 136.5 |
| exit angle [2δ](°) | 81.3 |
| incident height [hF] | 0.68 |
| exit height [hR] | 0.687 |
| maximum image height [IH] | 1.500 |

TABLE 5-continued

| | value standardized with image height |
|---|---|
| *TL | 2.425 |
| *hF | 0.453 |
| *hR | 0.458 |
| *|f1| | 0.401 |
| *sum | 1.985 |

The optical system has a lens construction composed of six lenses in four groups. The second lens group G2 is composed of a doublet made up of a positive lens element G2a and a negative lens element G2b. The third lens group G3 is composed of a doublet made up of a positive lens element G3a and a negative lens element G3b. The total length TL of the optical system is 3.638 mm, the lens thickness "sum" is 2.978 mm, the incident height hF is 0.680 mm, the exit height hR is 0.687 mm, when the maximum image height IH is 1.5 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "*|f1|" obtained by standardizing the absolute value |f1| of the focal length f1 of the first lens group G1 with the maximum image height IH, and "sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 6

Figure 15:
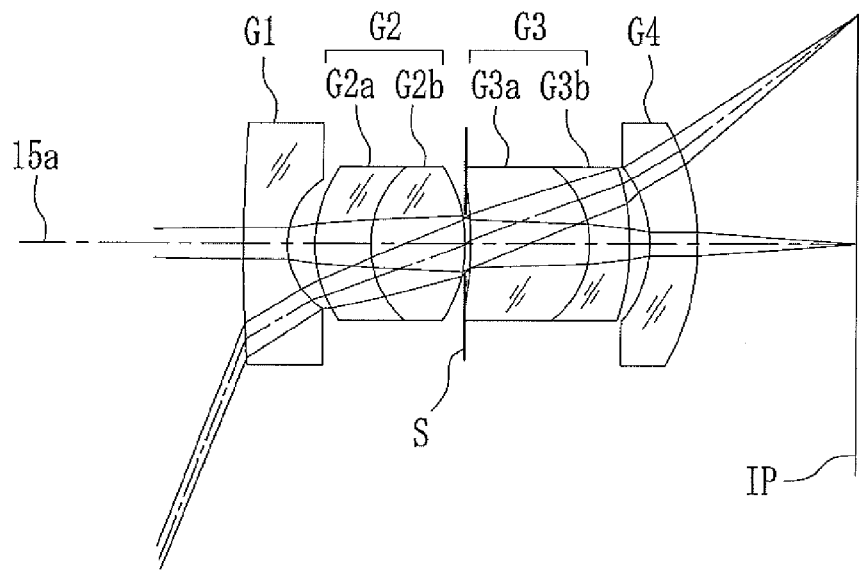
FIG. 15 is a lens construction diagram of an optical system of an example 6 of the present invention.
Figure 16:
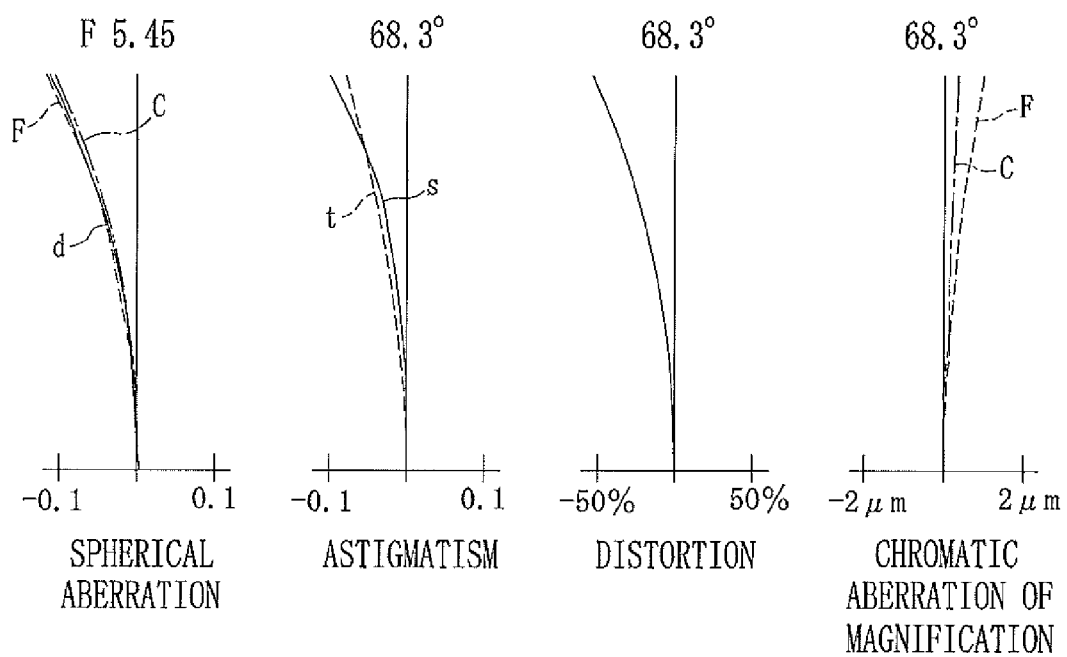
FIG. 16 is an aberration diagram of the example 6.

The imaging optical system 15 has a lens construction composed of six lenses in four groups as shown in FIG. 15. The optical system data is shown in table 6. The aberration characteristics are shown in FIG. 16.

TABLE 6

| Surface No. | r | d | nd | νd | | |
|---|---|---|---|---|---|---|
| 1 | 12.539 | 0.300 | 1.88300 | 40.80 | f1 | −0.583 |
| 2 | 0.489 | 0.175 | | | f2 | 0.684 |
| 3 | 0.859 | 0.386 | 1.73800 | 32.26 | f3 | 4.578 |
| 4 | 0.677 | 0.609 | 1.88300 | 40.80 | f4 | −2.756 |
| 5 | −0.979 | 0.000 | | | fF | 0.935 |
| 6 | aperture stop | 0.030 | | | D1 | 1.470 |
| | | | | | fR | −5.547 |
| 7 | −7.425 | 0.800 | 1.80100 | 34.97 | D2 | 1.530 |
| 8 | −0.599 | 0.250 | 1.92286 | 18.90 | | |
| 9 | −1.864 | 0.150 | | | | |
| 10 | −0.807 | 0.300 | 1.64769 | 33.79 | | |
| 11 | −1.688 | | | | | |

| | |
|---|---|
| focal length [f] | 1.247 |
| back length [BL] | 0.903 |
| lens thickness [sum] | 3.00 |
| total length [TL] | 3.903 |
| field angle [2ω](°) | 136.5 |
| exit angle [2δ](°) | 73.1 |
| incident height [hF] | 0.628 |
| exit height [hR] | 0.623 |
| maximum image height [IH] | 1.500 |

TABLE 6-continued

| | value standardized with image height |
|---|---|
| *TL | 2.602 |
| *hF | 0.419 |
| *hR | 0.415 |
| *|f1| | 0.389 |
| *sum | 2.000 |

The optical system has a lens construction composed of six lenses in four groups. The second lens group G2 is composed of a doublet made up of a negative lens element G2a and a positive lens element G2b. The third lens group G3 is composed of a doublet made up of a positive lens element G3a and a negative lens element G3b. The total length TL of the optical system is 3.903 mm, the lens thickness "sum" is 3.00 mm, the incident height hF is 0.628 mm, the exit height hR is 0.623 mm, when the maximum image height IH is 1.5 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "*|f1|" obtained by standardizing the absolute value |f1| of the focal length f1 of the first lens group G1 with the maximum image height IH, and "sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 7

Figure 17:
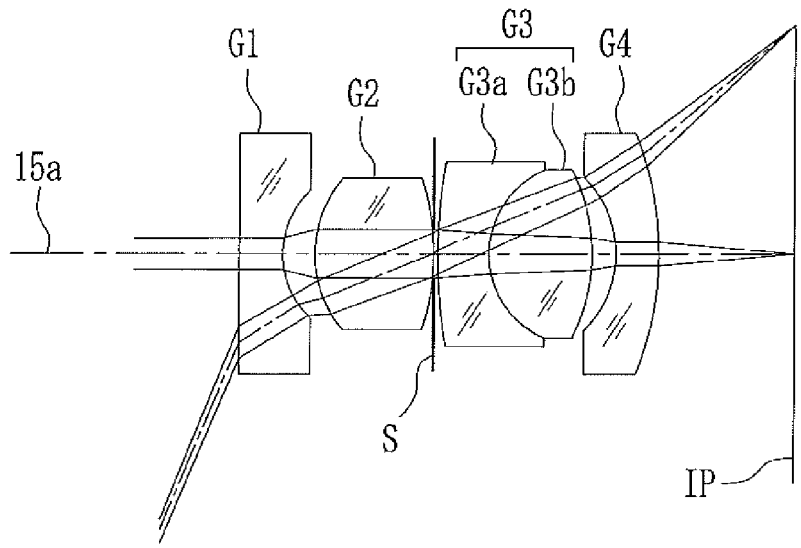
FIG. 17 is a lens construction diagram of an optical system of an example 7 of the present invention.
Figure 18:
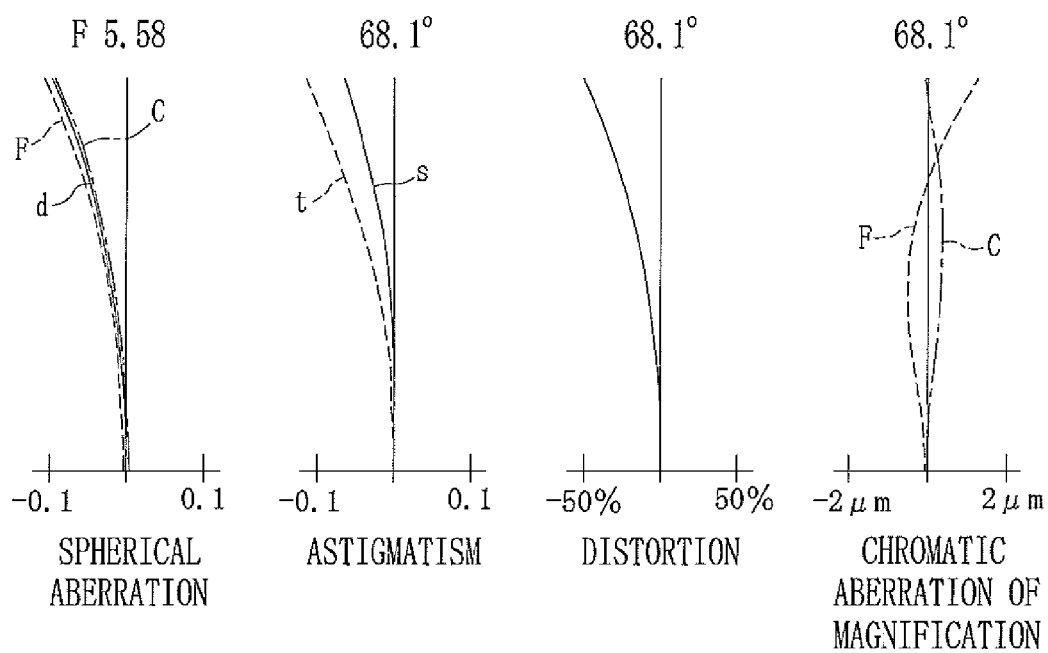
FIG. 18 is an aberration diagram of the example 7.

The imaging optical system 15 has a lens construction composed of five lenses in four groups as shown in FIG. 17. The optical system data is shown in table 7. The aberration characteristics are shown in FIG. 18.

TABLE 7

| Surface No. | r | d | nd | νd | | |
|---|---|---|---|---|---|---|
| 1 | 0.000 | 0.300 | 1.88300 | 40.80 | f1 | −0.592 |
| 2 | 0.523 | 0.200 | | | f2 | 0.732 |
| 3 | 0.714 | 0.800 | 1.80610 | 40.92 | f3 | 1.427 |
| 4 | −1.706 | 0.000 | | | f4 | −1.763 |
| 5 | aperture stop | 0.030 | | | fF | 2.036 |
| | | | | | D1 | 1.300 |
| 6 | 2.780 | 0.352 | 1.84666 | 23.78 | fR | 4.378 |
| 7 | 0.600 | 0.683 | 1.77030 | 47.40 | D2 | 1.530 |
| 8 | −1.299 | 0.165 | | | | |
| 9 | −0.686 | 0.300 | 1.67300 | 38.15 | | |
| 10 | −1.913 | | | | | |

| | |
|---|---|
| focal length [f] | 1.211 |
| back length [BL] | 0.734 |
| lens thickness [sum] | 2.83 |
| total length [TL] | 3.564 |
| field angle [2ω](°) | 136.3 |
| exit angle [2δ](°) | 79.6 |
| incident height [hF] | 0.581 |
| exit height [hR] | 0.663 |
| maximum image height [IH] | 1.500 |

TABLE 7-continued

| | value standardized with image height |
|---|---|
| *TL | 2.376 |
| *hF | 0.387 |
| *hR | 0.442 |
| *\|f1\| | 0.395 |
| *sum | 1.887 |

The optical system has a lens construction composed of five lenses in four groups. The third lens group G3 is composed of a doublet made up of a negative lens element G3a and a positive lens element G3b. The total length TL of the optical system is 3.564 mm, the lens thickness "sum" is 2.83 mm, the incident height hF is 0.581 mm, the exit height hR is 0.663 mm, when the maximum image height IH is 1.5 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "|f1|" obtained by standardizing the absolute value |f1| of the focal length f1 of the first lens group G1 with the maximum image height IH, and "*sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 8

Figure 19:
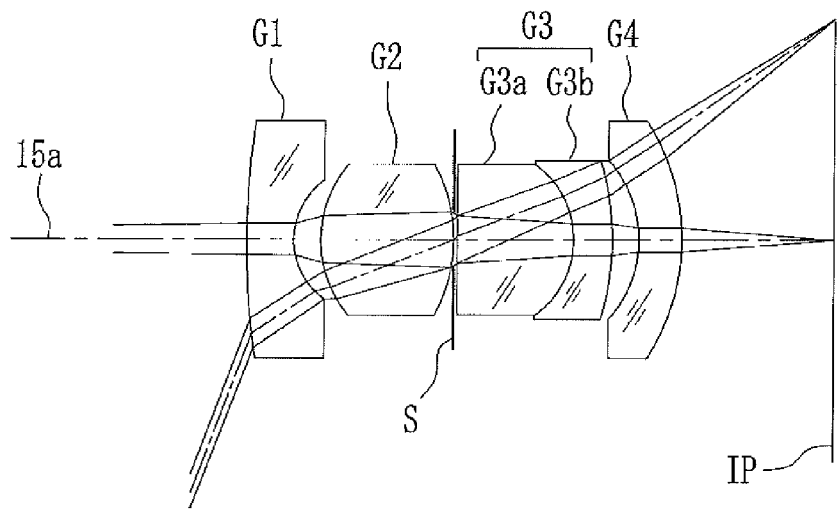
FIG. 19 is a lens construction diagram of an optical system of an example 8 of the present invention.
Figure 20:
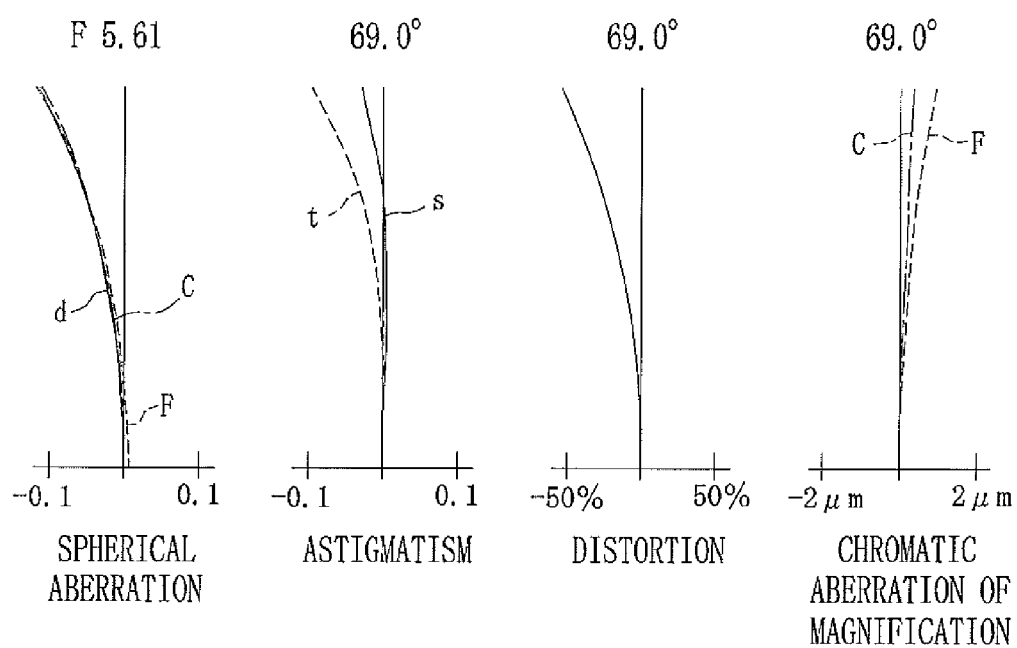
FIG. 20 is an aberration diagram of the example 8.

The imaging optical system 15 has a lens construction composed of five lenses in four groups as shown in FIG. 19. The optical system data is shown in table 8. The aberration characteristics are shown in FIG. 20.

TABLE 8

| Surface No. | r | d | nd | νd | | |
|---|---|---|---|---|---|---|
| 1 | 9.605 | 0.300 | 1.88300 | 40.80 | f1 | −0.565 |
| 2 | 0.467 | 0.200 | | | f2 | 0.688 |
| 3 | 0.782 | 0.900 | 1.80400 | 46.57 | f3 | 4.737 |
| 4 | −0.922 | 0.000 | | | f4 | −3.699 |
| 5 | aperture stop | 0.030 | | | fF | 1.058 |
| | | | | | D1 | 1.400 |
| 6 | 0.000 | 0.800 | 1.72000 | 50.23 | fR | −12.895 |
| 7 | −0.600 | 0.266 | 1.92286 | 20.88 | D2 | 1.569 |
| 8 | −1.759 | 0.173 | | | | |
| 9 | −0.818 | 0.300 | 1.58144 | 40.75 | | |
| 10 | −1.498 | | | | | |

| focal length [f] | 1.241 |
|---|---|
| back length [BL] | 0.862 |
| lens thickness [sum] | 2.969 |
| total length [TL] | 3.831 |
| field angle [2ω](°) | 137.9 |
| exit angle [2δ](°) | 71.3 |
| incident height [hF] | 0.624 |
| exit height [hR] | 0.659 |
| maximum image height [IH] | 1.500 |

TABLE 8-continued

| | value standardized with image height |
|---|---|
| *TL | 2.554 |
| *hF | 0.416 |
| *hR | 0.439 |
| *\|f1\| | 0.376 |
| *sum | 1.979 |

The optical system has a lens construction composed of five lenses in four groups. The third lens group G3 is composed of a doublet made up of a positive lens element G3a and a negative lens element G3b. The total length TL of the optical system is 3.831 mm, the lens thickness "sum" is 2.969 mm, the incident height hF is 0.624 mm, the exit height hR is 0.659 mm, when the maximum image height IH is 1.5 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "|f1|" obtained by standardizing the absolute value |f1| of the focal length f1 of the first lens group G1 with the maximum image height IH, and "*sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 9

Figure 21:
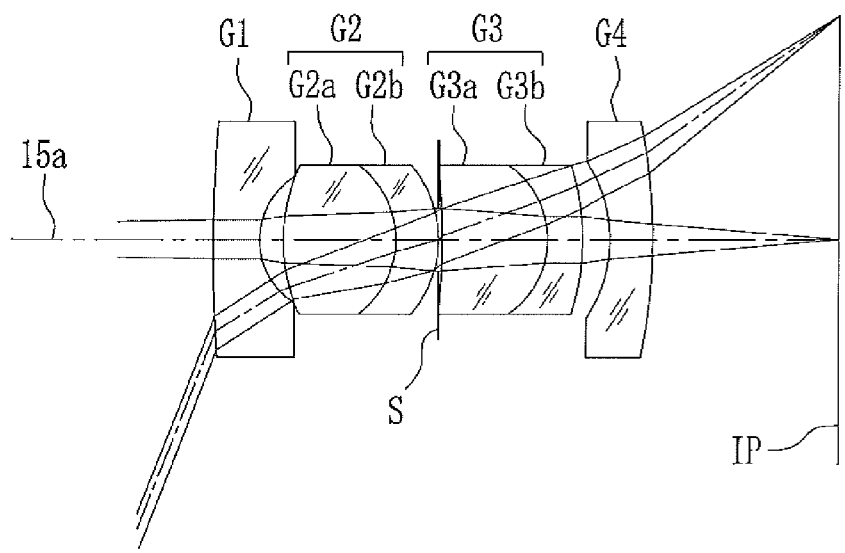
FIG. 21 is a lens construction diagram of an optical system of an example 9 of the present invention.
Figure 22:
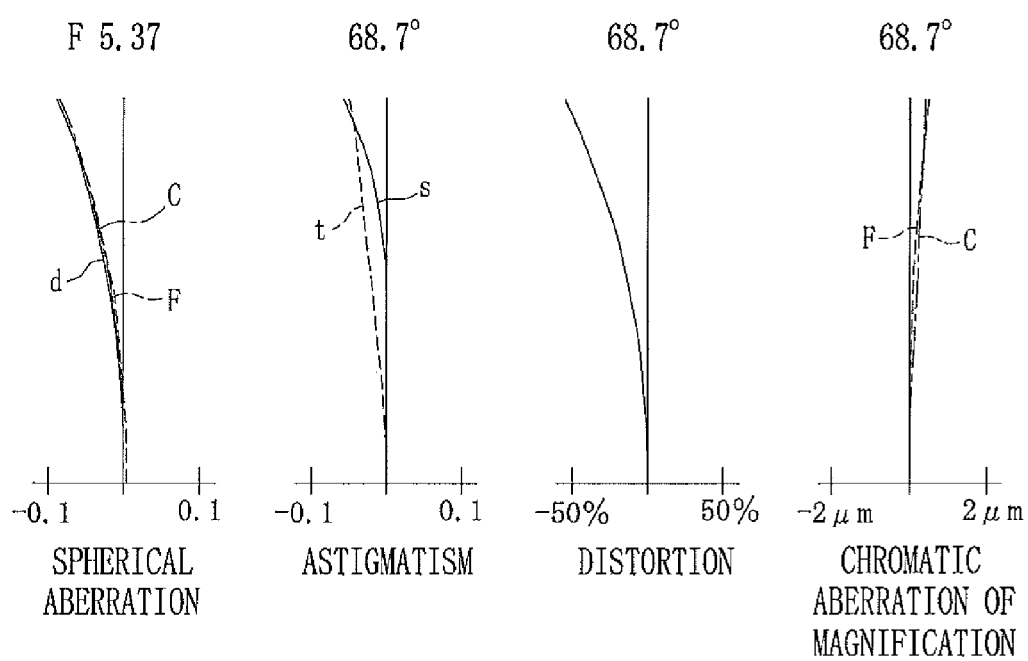
FIG. 22 is an aberration diagram of the example 9.

The imaging optical system 15 has a lens construction composed of six lenses in four groups as shown in FIG. 21. The optical system data is shown in table 9. The aberration characteristics are shown in FIG. 22.

TABLE 9

| Surface No. | r | d | nd | νd | | |
|---|---|---|---|---|---|---|
| 1 | 9.814 | 0.300 | 1.88300 | 40.80 | f1 | −0.565 |
| 2 | 0.468 | 0.161 | | | f2 | 0.702 |
| 3 | 1.054 | 0.795 | 1.91082 | 35.25 | f3 | 3.657 |
| 4 | −0.579 | 0.268 | 1.92286 | 20.88 | f4 | −2.378 |
| 5 | −0.841 | 0.000 | | | fF | 0.905 |
| 6 | aperture stop | 0.030 | | | D1 | 1.524 |
| | | | | | fR | −5.147 |
| 7 | −4.258 | 0.724 | 1.75501 | 51.16 | D2 | 1.475 |
| 8 | −0.556 | 0.250 | 1.92286 | 20.88 | | |
| 9 | −1.356 | 0.171 | | | | |
| 10 | −0.955 | 0.300 | 1.58144 | 40.75 | | |
| 11 | −3.443 | | | | | |

| focal length [f] | 1.249 |
|---|---|
| back length [BL] | 1.101 |
| lens thickness [sum] | 3.00 |
| total length [TL] | 4.10 |
| field angle [2ω](°) | 137.5 |
| exit angle [2δ](°) | 70.2 |
| incident height [hF] | 0.622 |
| exit height [hR] | 0.580 |
| maximum image height [IH] | 1.500 |

TABLE 9-continued

|  | value standardized with image height |
|---|---|
| *TL | 2.733 |
| *hF | 0.415 |
| *hR | 0.387 |
| *│f1│ | 0.377 |
| *sum | 2.000 |

The optical system has a lens construction composed of six lenses in four groups. The second lens group G2 is composed of a doublet made up of a positive lens element G2a and a negative lens element G2b. The third lens group G3 is composed of a doublet made up of a positive lens element G3a and a negative lens element G3b. The total length TL of the optical system is 4.10 mm, the lens thickness "sum" is 3.00 mm, the incident height hF is 0.622 mm, the exit height hR is 0.580 mm, when the maximum image height IH is 1.50 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "*│f1│" obtained by standardizing the absolute value │f1│ of the focal length f1 of the first lens group G1 with the maximum image height IH, and "sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

EXAMPLE 10

Figure 23:
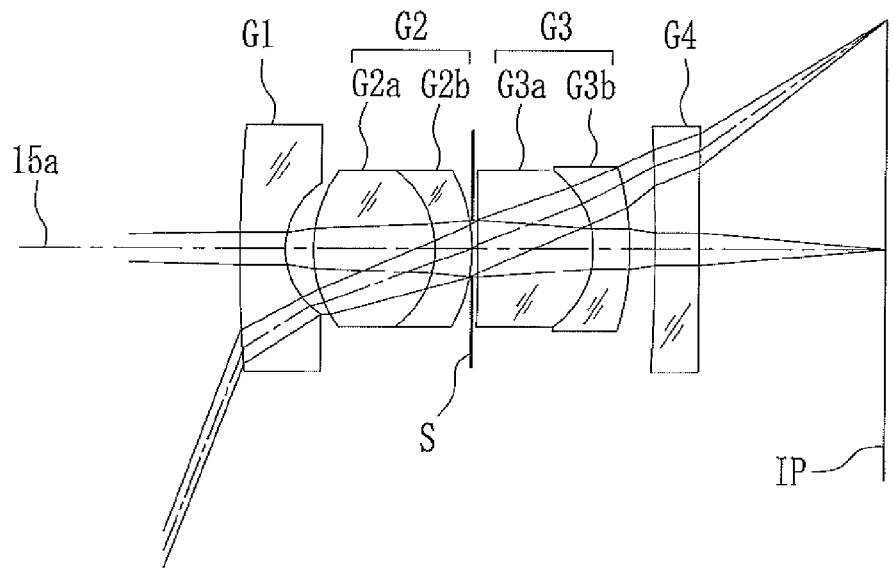
FIG. 23 is a lens construction diagram of an optical system of an example 10 of the present invention.
Figure 24:
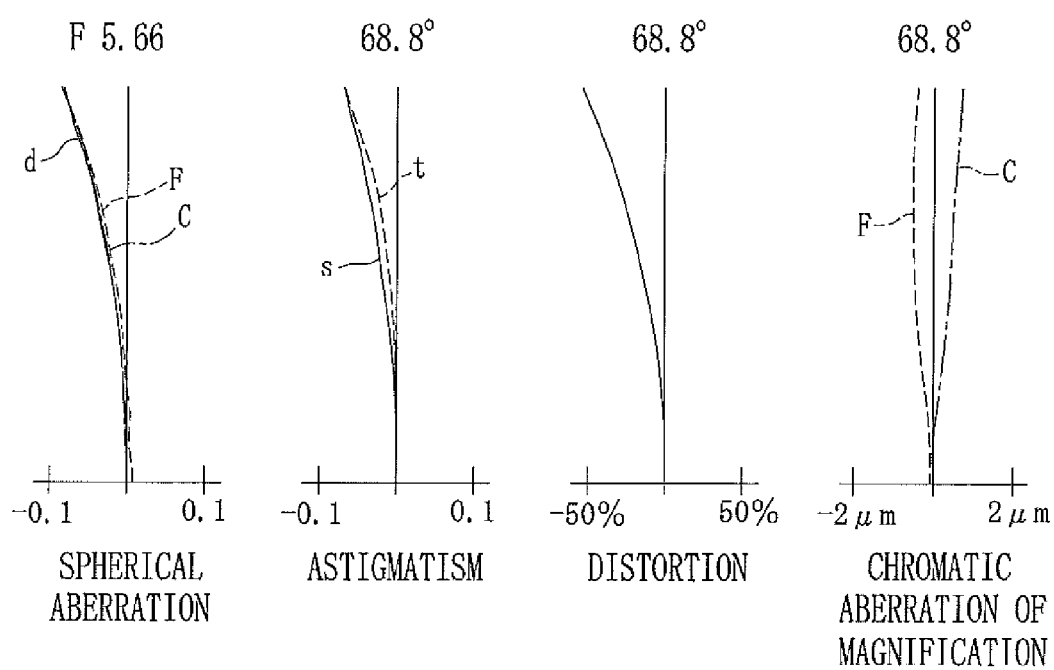
FIG. 24 is an aberration diagram of the example 10.

The imaging optical system 15 has a lens construction composed of six lenses in four groups as shown in FIG. 23. The optical system data is shown in table 10. The aberration characteristics are shown in FIG. 24.

TABLE 10

| Surface No. | r | d | nd | vd | | |
|---|---|---|---|---|---|---|
| 1 | 17.339 | 0.300 | 1.88300 | 40.80 | f1 | −0.596 |
| 2 | 0.507 | 0.168 | | | f2 | 0.730 |
| 3 | 0.838 | 0.800 | 1.83400 | 37.34 | f3 | 29.651 |
| 4 | −0.600 | 0.250 | 1.92286 | 20.88 | f4 | −10.519 |
| 5 | −0.899 | 0.000 | | | fF | 1.053 |
| 6 | aperture stop | 0.030 | | | D1 | 1.518 |
| | | | | | fR | −13.768 |
| 7 | −6.690 | 0.752 | 1.61772 | 49.81 | D2 | 1.482 |
| 8 | −0.600 | 0.250 | 1.92286 | 20.88 | | |
| 9 | −1.580 | 0.150 | | | | |
| 10 | −6.732 | 0.300 | 1.64000 | 60.08 | | |
| 11 | 0.000 | | | | | |
| focal length [f] | | | | 1.272 | | |
| back length [BL] | | | | 1.045 | | |

TABLE 10-continued

| lens thickness [sum] | 3.00 |
|---|---|
| total length [TL] | 4.045 |
| field angle [2ω](°) | 137.6 |
| exit angle [2δ](°) | 70 |
| incident height [hF] | 0.646 |
| exit height [hR] | 0.652 |
| maximum image height [IH] | 1.500 |

|  | value standardized with image height |
|---|---|
| *TL | 2.697 |
| *hF | 0.431 |
| *hR | 0.435 |
| *│f1│ | 0.398 |
| *sum | 2.000 |

The optical system has a lens construction composed of six lenses in four groups. The second lens group G2 is composed of a doublet made up of a positive lens element G2a and a negative lens element G2b. The third lens group G3 is composed of a doublet made up of a positive lens element G3a and a negative lens element G3b. The total length TL of the optical system is 4.045 mm, the lens thickness "sum" is 3.00 mm, the incident height hF is 0.646 mm, the exit height hR is 0.652 mm, when the maximum image height IH is 1.50 mm. Hence, the total length and the outer diameter fall within appropriate ranges in a manner similar to the above examples. Thus, the wide angle imaging optical system, suitable for an observation optical system of the endoscope, is obtained. The values "*TL" obtained by standardizing the total length TL with the maximum image height IH, "*hF" obtained by standardizing the incident height hF with the maximum image height IH, "*hR" obtained by standardizing the exit height hR with the maximum image height IH, "*│f1│" obtained by standardizing the absolute value │f1│ of the focal length f1 of the first lens group G1 with the maximum image height IH, and "*sum" obtained by standardizing the lens thickness "sum" with the maximum image height IH satisfy the conditions specified by the expressions (1) to (5), respectively. Thus, the imaging optical system is sufficiently downsized relative to the image size and various aberrations are corrected.

Figure 25:
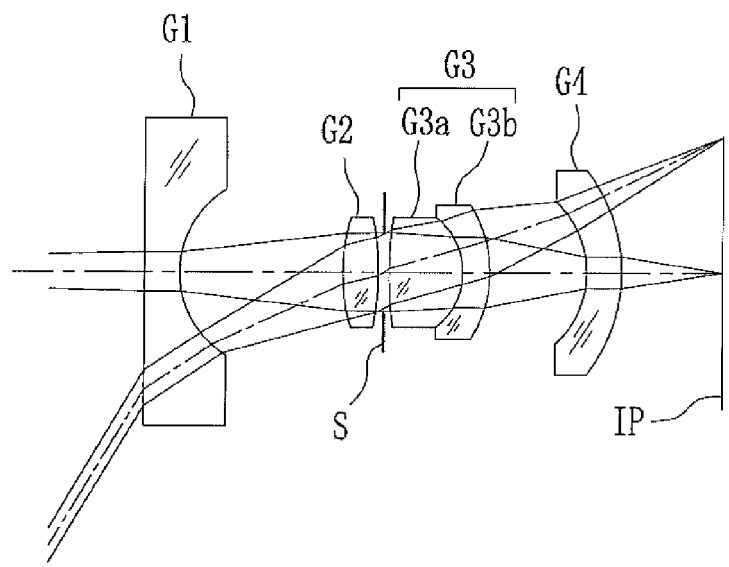
FIG. 25 is a lens construction diagram of a comparative example.
Figure 26:
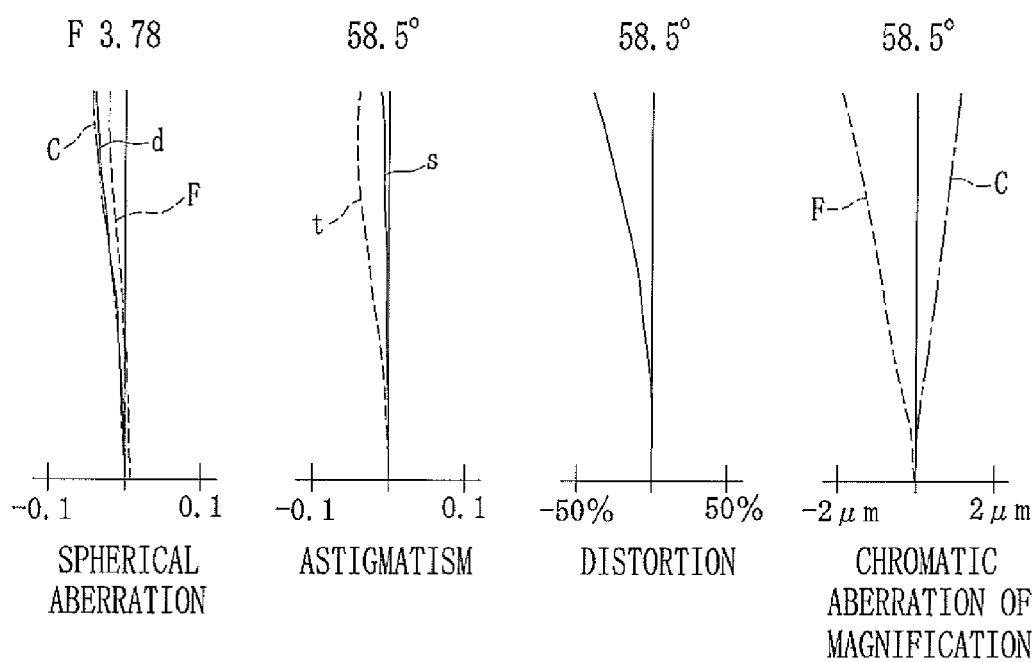
FIG. 26 is an aberration diagram of the comparative example 1.

Note that FIG. 25 shows a comparative example 1 using an optical system disclosed in Example 1 of U.S. Pat. No. 4,674,844 (corresponding to Japanese Examined Patent Application Publication No. 6-48327). The comparative example 1 is similar to the above examples 1 to 10 of the present invention in that the optical system is composed of four groups, first lens group G1, second lens group G2, third lens group G3, and fourth lens group G4, arranged in this order from the object side, with the concave-convex-convex-concave power distribution and that the aperture stop S is provided between the second lens group G2 and the third lens group G3. The aberration characteristics of the imaging optical system of the comparative example 1 are shown in FIG. 26.

Table 11 shows optical system data of the comparative examples including the comparative example 1 in FIG. 25. The optical system data of the comparative examples 2 to 7 in the table 11 corresponds to that of the imaging optical system of Examples 2 to 7 in the U.S. Pat. No. 4,674,844.

TABLE 11

|  | CE. 1 | CE. 2 | CE. 3 | CE. 4 | CE. 5 | CE. 6 | CE. 7 |
|---|---|---|---|---|---|---|---|
| [f] | 1.00 | 1.00 | 1.00 | 1.00 | 1.00 | 1.003 | 1.00 |
| [BL] | 0.668 | 0.419 | 0.277 | 0.377 | 0.384 | 0.671 | 0.801 |

TABLE 11-continued

|  | CE. 1 | CE. 2 | CE. 3 | CE. 4 | CE. 5 | CE. 6 | CE. 7 |
|---|---|---|---|---|---|---|---|
| [sum] | 3.617 | 3.982 | 3.924 | 3.694 | 4.069 | 4.574 | 4.657 |
| [*sum] | [3.6026] | [3.2904] | [3.2936] | [3.6607] | [3.6870] | [4.170] | [4.1801] |
| [TL] | 4.285 | 4.401 | 4.201 | 4.071 | 4.453 | 5.245 | 5.458 |
| [*TL] | [4.268] | [3.637] | [3.526] | [4.034] | [4.035] | [4.782] | [4.899] |
| [2ω] | 117.1 | 115.6 | 114.9 | 117.7 | 101.7 | 98.6 | 99.4 |
| [2δ] | 52.7 | 79.2 | 78.6 | 52.3 | 60.5 | 48.3 | 46.1 |
| [hF] | 0.882 | 1.174 | 1.02 | 0.91 | 0.97 | 1.165 | 1.235 |
| [*hF] | [0.878] | [0.970] | [0.856] | [0.902] | [0.879] | [1.062] | [1.109] |
| [hR] | 0.560 | 0.676 | 0.779 | 0.723 | 0.683 | 0.642 | 0.642 |
| [*hR] | [0.558] | [0.559] | [0.654] | [0.716] | [0.619] | [0.585] | [0.576] |
| [IH] | 1.004 | 1.2102 | 1.1914 | 1.009 | 1.1036 | 1.0969 | 1.1141 |

Abbreviations are the same as those in the above examples. ([f]: focal length, [BL]: back length, [sum]: lens thickness, [TL]: total length, [2ω]: field angle (degree), [2δ]: exit angle (degree), [hF]: incident height, [hR]: exit height, [IH]: maximum image height, CE: comparative example)

As shown in the table 11, the maximum image height IH varies in a range of 1.004 to 1.2102. Although the maximum image height IH is smaller than the maximum image height 1.500 of the examples of the present invention, the total length TL of the optical system, the lens thickness "sum", the incident height hF, and the exit height hR are greater than those of the examples of the present invention. Hence, the total length TL and the lens thickness "sum" of the imaging optical system of each comparative example are large relative to the image size. Accordingly, the outer diameter becomes significantly large. Thus, downsizing of the imaging optical system is insufficient.

In the table 11, a value in parentheses [ ] shows a piece of the optical data standardized with the maximum image height IH. In each of the comparative examples 1 to 7, the value "*TL" is within a range of 3.526 to 4.899 and does not satisfy the expression (1). Thus, the total length of the optical system is not shortened sufficiently relative to the size of the image plane. The value "*hF" is greater than or equal to 0.85 and does not satisfy the expression (2). The value "*hR" is 0.558 at the smallest and does not satisfy the expression (3), but the outer diameter of the fourth lens group G4 can still be reduced because the value only slightly exceeds the upper limit. In this case, however, the value "*hF" is 0.878, so that the outer diameter of the first lens group G1 cannot be reduced sufficiently. Hence, the diameter of the entire imaging optical system cannot be reduced. The value "*sum" exceeds 3.29, which is large and does not satisfy the expression (5). Thus, the lens thickness is not reduced sufficiently.

The imaging optical system of the present invention has a large exit angle 2δ. The exit angle 2δ in each table refers to an angle between a pair of principal rays exiting from the surface of the fourth lens group G4, proximate to the image plane, symmetrically about the optical axis 15a. Particularly, the exit angle 2δ is the angle between the pair of principal rays exiting toward the respective maximum image height positions, located symmetrically about the optical axis 15a, on the image plane IP. Hence, an angle between the principal ray directed to one of the maximum image height positions and the optical axis 15a, that is, the angle of incidence of the principal ray on the maximum image height position on the image plane IP is δ. The angle δ of incidence is the maximum angle of incidence of the principal ray on the image sensor 16.

As described above, photoelectric conversion efficiency of the image sensor 16 decreases as the angle of incidence of the principal ray on the image sensor 16 increases. Restrictions on the angle of incidence of the principal rays are significantly reduced by using the organic CMOS sensor as the image sensor 16. Hence, as described in each example of the present invention, the optical system is put into practical use even if the maximum angle δ of incidence increases to a range of 35° to 47.75°. When the maximum angle δ of incidence of the principal ray on the image sensor 16 is rather small, the back-illumination type CMOS sensor can be used instead of the organic CMOS sensor. In most of the comparative examples 1 to 7, the maximum angle δ of incidence of the principal ray is reduced to 23°-30°, which restricts the design of the imaging optical system.

The present invention has been described using the examples 1 to 10 each with the lenses only having spherical surfaces. Alternatively, the imaging optical system of the present invention includes one or more aspheric surfaces. In addition to the use in the rigid tip section of the endoscope, the imaging optical system of the present invention can be used in mobile information terminals such as mobile phones, stationary surveillance cameras, and vehicle-mounted cameras which require reduction in size relative to the image size. The present invention can be implemented as the imaging devices having the imaging optical systems with the above-described characteristics integrated with various types of image sensors.

Various changes and modifications are possible in the present invention and may be understood to be within the present invention.

What is claimed is:

1. An imaging optical system comprising:
    a negative first lens group;
    a positive second lens group;
    a positive third lens group;
    a negative fourth lens group, the first to fourth lens groups are arranged in this order from an object side; and
    an aperture stop provided between the second and third lens groups;
    the imaging optical system satisfying expressions (1) to (5):

$$2.00 < TL/IH < 3.00 \tag{1}$$

$$0.37 < hF/IH < 0.5 \tag{2}$$

$$0.37 < hR/IH < 0.5 \tag{3}$$

$$3.5 < |f1/IH| < 4.5 \tag{4}$$

$$1.8 < \text{sum}/IH < 2.1 \tag{5}$$

wherein "IH" represents a maximum image height, "TL" represents a total length of "sum" and a back focal length, the back focal length being a distance from a rearmost lens plane and a paraxial image plane, the "sum" represents the distance from the most object side lens surface to the most image side lens surface, "hF" represents an incident height of a principal ray, corresponding to the maximum image height "IH", at a surface proximate to the object side, "hR" represents an exit height of the principal ray at a surface proximate to an image plane, and "f1" represents a focal length of the first lens group, and the imaging optical system is a fixed local length system.

2. The imaging optical system of claim 1, wherein the first lens group consists of a single lens with a concave surface facing the image plane, and the fourth lens group consist of a single lens with a concave surface facing the object side, and at least one of the second lens group and the third lens group consists of a doublet made up of a positive lens element and a negative lens element attached together.

3. An imaging device comprising:
an imaging optical system of claim 1; and
an image sensor disposed on an image plane of the imaging optical system, the image sensor being a back-illumination type CMOS image sensor or an organic CMOS image sensor.

4. An imaging device comprising:
an imaging optical system of claim 2; and
an image sensor disposed on an image plane of the imaging optical system, the image sensor being a back-illumination type CMOS image sensor or an organic CMOS image sensor.

5. The imaging device of claim 3, wherein the imaging device is incorporated in a distal end portion of an endoscope for imaging a body cavity.

6. The imaging device of claim 4, wherein the imaging device is incorporated in a distal end portion of an endoscope for imaging a body cavity.

7. The imaging optical system of claim 1, wherein $2.211 < TL/IH < 3.00$ is satisfied.

* * * * *